US009877983B2

(12) United States Patent
Onsoyen et al.

(10) Patent No.: US 9,877,983 B2
(45) Date of Patent: *Jan. 30, 2018

(54) USE OF ALGINATE OLIGOMERS IN COMBATING BIOFILMS

(71) Applicant: ALGIPHARMA AS, Sandvika, Baerum (NO)

(72) Inventors: Edvar Onsoyen, Sandvika (NO); Rolf Myrvold, Sandvika (NO)

(73) Assignee: ALGIPHARMA AS, Sandvika, Baerum (NO)

(*) Notice: Subject to any disclaimer, the term of this patent is extended or adjusted under 35 U.S.C. 154(b) by 0 days.

This patent is subject to a terminal disclaimer.

(21) Appl. No.: 14/221,691

(22) Filed: Mar. 21, 2014

(65) Prior Publication Data
US 2014/0205643 A1 Jul. 24, 2014

Related U.S. Application Data

(63) Continuation of application No. 12/745,058, filed as application No. PCT/GB2008/003607 on Oct. 24, 2008, now Pat. No. 8,680,072.

(60) Provisional application No. 60/996,611, filed on Nov. 27, 2007.

(51) Int. Cl.
| A61K 31/734 | (2006.01) |
| A61K 8/73 | (2006.01) |
| A61Q 19/00 | (2006.01) |
| A61K 8/66 | (2006.01) |
| A61K 31/65 | (2006.01) |
| A01N 43/16 | (2006.01) |
| A61K 38/48 | (2006.01) |
| A61K 45/06 | (2006.01) |
| A61K 31/7036 | (2006.01) |
| A01N 63/02 | (2006.01) |
| A01N 65/03 | (2009.01) |
| A61Q 11/00 | (2006.01) |
| A61Q 17/00 | (2006.01) |

(52) U.S. Cl.
CPC ........... A61K 31/734 (2013.01); A01N 43/16 (2013.01); A01N 63/02 (2013.01); A01N 65/03 (2013.01); A61K 8/66 (2013.01); A61K 8/733 (2013.01); A61K 31/65 (2013.01); A61K 31/7036 (2013.01); A61K 38/4886 (2013.01); A61K 45/06 (2013.01); A61Q 11/00 (2013.01); A61Q 17/005 (2013.01); A61Q 19/007 (2013.01)

(58) Field of Classification Search
CPC ...... A61K 31/734; A61K 45/06; A61K 8/733; A61K 38/4886; A61K 8/66; A61Q 19/007; A01N 43/16
USPC .......... 514/54, 40; 424/94.67, 411
See application file for complete search history.

(56) References Cited

U.S. PATENT DOCUMENTS

| 4,225,592 | A | 9/1980 | Lakatos et al. |
| 5,166,137 | A | 11/1992 | Otterlei et al. |
| 5,169,840 | A | 12/1992 | Otterlei et al. |
| 5,192,362 | A | 3/1993 | Harvey et al. |
| 5,683,991 | A | 11/1997 | Guggenbichler et al. |
| 6,121,441 | A | 9/2000 | Simensen et al. |
| 6,339,075 | B1 | 1/2002 | King et al. |
| 6,395,307 | B1 | 5/2002 | Banning et al. |
| 6,407,226 | B1 | 6/2002 | Simensen et al. |
| 6,641,740 | B2 | 11/2003 | Cornelius et al. |
| 7,208,141 | B2 | 4/2007 | Montgomery |
| 7,671,100 | B2 | 3/2010 | Gaserod et al. |
| 7,671,101 | B2 | 3/2010 | Gaserod et al. |
| 7,671,102 | B2 | 3/2010 | Gaserod et al. |
| 7,674,837 | B2 | 3/2010 | Gaserod et al. |
| 7,758,856 | B2 | 7/2010 | Hughes et al. |
| 7,776,839 | B2 | 8/2010 | Del Buono et al. |
| 7,790,699 | B2 | 9/2010 | Melvik et al. |
| 8,680,072 | B2* | 3/2014 | Onsoyen ............... A01N 43/16 514/54 |
| 8,815,831 | B2* | 8/2014 | Onsoyen ............ A61K 31/7048 514/23 |
| 2003/0013678 | A1 | 1/2003 | Lang et al. |
| 2003/0022863 | A1 | 1/2003 | Stahl et al. |
| 2003/0224070 | A1 | 12/2003 | Sweazy et al. |
| 2004/0073964 | A1 | 4/2004 | Ellington et al. |

(Continued)

FOREIGN PATENT DOCUMENTS

| CN | 1053546 A | 8/1991 |
| DE | 268865 A1 | 1/1987 |

(Continued)

OTHER PUBLICATIONS

Mandel et al. Infectious Diseases Society of America/American Thoracic Society Consensus Guidelines on the Management of Community-Acquired Pneumonia in Adults. Clinical Infectious Diseases 44:S27-S72, 2007.*
Fridkin, S.K. and Jarvis, W.R. 1996 "Epidemiology of Nosocomial Fungal Infections" Clinical Microbiology Reviews 9: 499-511.
Sakai, S. et al. 2002 "Permeability of alginate/sol-gel synthesized aminopropyl-silicate/alginate membrane templated by calcium-alginate gel" J Membrane Sci 205: 183-189.
Alkawash, M.A. et al. 2006 "Alginate lyase enhances antibiotic killing of mucoid Pseudomonas aeruginosa in biofilms" APMIS, 114(2):131-138.
Appleman, M.D. et al. 2000 "In vitro activities of nontraditional antimicrobials against mutiresistant Acinetobacter baumannii strains isolated in an intensive care unit outbreak" Antimicrobial Agents and Chemotherapy 44: 1035-1040.

(Continued)

Primary Examiner — Yih-Horng Shiao
(74) Attorney, Agent, or Firm — Knobbe, Martens Olson & Bear, LLP

(57) ABSTRACT

The invention provides a method for combating biofilm, said method comprising contacting a biofilm with an alginate oligomer. The biofilm may be on an animate or inanimate surface and both medical and non-medical uses and methods are provided. In one aspect the invention provides an alginate oligomer for use in the treatment or prevention of a biofilm infection in a subject. In another aspect the method can be used to combat biofilms, on abiotic surfaces, e.g. for disinfection and cleaning purposes.

27 Claims, 11 Drawing Sheets

(56) References Cited

U.S. PATENT DOCUMENTS

| | | | |
|---|---|---|---|
| 2004/0224922 A1 | 11/2004 | King | |
| 2005/0058744 A1* | 3/2005 | Steinberg | A23G 1/325 426/3 |
| 2006/0121019 A1* | 6/2006 | Budny | A61K 8/64 424/94.61 |
| 2007/0237812 A1 | 10/2007 | Patel et al. | |
| 2008/0085295 A1* | 4/2008 | Melvik | A61K 9/0024 424/423 |
| 2008/0188568 A1 | 8/2008 | Suvanprakorn et al. | |
| 2010/0068290 A1 | 3/2010 | Ziegler et al. | |
| 2010/0305062 A1 | 12/2010 | Onsoyen et al. | |
| 2012/0308632 A1 | 12/2012 | Ghigo et al. | |

FOREIGN PATENT DOCUMENTS

| | | |
|---|---|---|
| DE | 10221748 A1 | 12/2003 |
| EP | 0324720 A1 | 7/1989 |
| EP | 0506326 A2 | 9/1992 |
| EP | 0590746 A1 | 4/1994 |
| EP | 0807631 A1 | 11/1997 |
| EP | 1234584 A1 | 8/2002 |
| EP | 1714660 A1 | 10/2006 |
| EP | 1745705 A1 | 1/2007 |
| FR | 7576 M | 3/1968 |
| GB | 1042379 | 9/1966 |
| GB | 2430881 A | 4/2007 |
| JP | H04-036228 A | 2/1992 |
| JP | 05-252970 | 10/1993 |
| JP | 09208472 | 8/1997 |
| JP | 2005145885 | 11/2003 |
| JP | 2008285431 | 5/2007 |
| KR | 20000032630 | 11/1998 |
| WO | WO 98/02488 A1 | 1/1988 |
| WO | WO 98/51710 A1 | 11/1988 |
| WO | WO 88/09794 A1 | 12/1988 |
| WO | WO 91/11205 A1 | 8/1991 |
| WO | WO 94/09124 A1 | 4/1994 |
| WO | WO 95/18145 A1 | 7/1995 |
| WO | WO 96/33164 A1 | 10/1996 |
| WO | WO 98/51342 A1 | 11/1998 |
| WO | WO 99/14312 A1 | 3/1999 |
| WO | WO 01/15672 A2 | 3/2001 |
| WO | WO 01/66084 A2 | 9/2001 |
| WO | WO 03/045402 A1 | 6/2003 |
| WO | WO 03/046199 A2 | 6/2003 |
| WO | WO 2004/011628 A1 | 2/2004 |
| WO | WO 2005/023176 A2 | 3/2005 |
| WO | WO 2005/030257 A2 | 4/2005 |
| WO | WO 2005/079210 A2 | 9/2005 |
| WO | WO 2006/120705 A2 | 11/2006 |
| WO | WO 2007/0039754 A1 | 4/2007 |
| WO | WO 2007/039760 A1 | 4/2007 |
| WO | WO 2008/006658 A1 | 1/2008 |
| WO | WO 2008/071407 A2 | 6/2008 |
| WO | WO 2008/082948 A2 | 7/2008 |
| WO | WO 2008/125828 A2 | 10/2008 |
| WO | WO 2009/018060 A1 | 2/2009 |
| WO | WO 2009/032433 A1 | 3/2009 |
| WO | WO 2009/068841 A2 | 6/2009 |
| WO | WO 2009/129525 A2 | 10/2009 |
| WO | WO 2010/069519 A1 | 6/2010 |
| WO | WO 2010/139956 A2 | 12/2010 |
| WO | WO 2010/139959 A2 | 12/2010 |

OTHER PUBLICATIONS

Araque-Calderon, Y. et al. 2008 "Antibiotic resistance patterns and SDS-PAGE protein profiles of *Burkholderia cepacia* complex isolates from nosocomial and environmental sources in Venezuela" *Med Sci Monit* 14: BR49-55.

Banning, D. et al. 1997 "Oscillatory and thermorheological characterization of alginate/mucin mixes" *Pharmacy and Pharmacology*, 49(Supp. 4) Poster 65.

Cannon, C. et al. 2006 "Emerging Pulmonary Infections in Cystic Fibrosis" *US Respiratory Disease*, pp. 27-29.

Cuenca, F.F. et al. 2003 "Actividad in vitro de azitromicina frente a aislamientos clinicos de *Acinetobacter baumannii*" *Rev Esp Quimioterap* 16: 204-208.

Dizbay, M. et al. 2009 "Nosocomial *Burkholderia cepacia* infections in a Turkish university hospital: a five-year surveillance" *J Infect Dev Ctries* 3: 273-277.

Djordjevic, D. et al. 2002 "Microtiter Plate Assay for Assessment of *Listeria monocytogenes* Biofilm Formation" *Appl Environ Microbiol* 68:2950-2958.

Donlan, R. M. et al. 2002 "Biofilms: Survival Mechanisms of clinically Relevant Microorganisms" *Clin. Mic. Rev.* 15(2):167-193.

Dunne, W.M. Jr. 2002 "Bacterial Adhesion: Seen Any good Biofilms Lately?" *Clinical Microbiology Reviews*, 15(2):155-166.

Emanuel, C. et al. 2012 "OligoG, a Novel Antimicrobial Alginate Oligosaccharide, Impedes Biofilm Development by Inhibition of Bacterial Motility" Poster No. F-2062 at IACC, San Francisco, Sep. 9-12, 2012.

Ertesvåg, H. et al. 1999 "Mannuronan C-5-Empimerases and Their Application for in Vitro and in Vivo Design of New Alginates Useful in Biotechnology" *Metabolic Engineering* 1:262-269.

Ferguson, D. et al. 2007 "Phenotypic, molecular and antibiotic resistance profiling of nosocomial *Pseudomonas aeruginosa* strains isolated from two Irish Hospitals" J Medicine vol. 1. (available online at: http://www.scientificjournals.org/journals2007/articles/1055.htm.

Flo, T. et al. 2000 "Involvement of CD14 and β2-Integrins in Activating Cells with Soluble and Particulate Lipopolysaccharides and Mannuronic Acid Polymers" *Infection and Immunity*, 68(12):6770-6776.

Fernandez-Cuenca, F. et al. 2003 "In vitro activity of Azithromycin in combination with Amikacin, Ceftazidime, Ciprofloxacin or Imipenem against clinical isolates of *Acinetobacter baumannii*" *Chemotherapy* 49: 24-26.

Gimmestad, M et al. 2003 "The *Pseudomonas fluorescens* AlgG Protein, but not its Mannuronan C-5-Epimerase Activity, is needed for Alginate Polymer Formation" *Journal of Bacteriology*, 185(12):3515-3523.

Gimmestad, M. et al. 2006 "Identification and Characterization of an *Azotobacter vinelandii* Type I Secretion System Responsible for Export of the AlgE-Type Mannuronan C-5-Epimerases" *Journal of Bacteriology*, 188(15):5551-5560.

Head, N.E. et al. 2004 "Cross-Sectional Analysis of Clinical and Environmental Isolates of *Pseudomonas aeruginosa*: Biofilm Formation, Virulence, and Genome Diversity" *Infection and Immunity* 72(1):133-144.

Hu, X. et al. 2005 "Antibacterial activity of lyase-depolymerized products of alginate" *Journal of Applied Phycology* 17: 57-60.

Jahr T.G. et al. 1997 "Induction of Tumor Necrosis Factor Production from Monocytes Stimulated with Mannuronic Acid Polymers and Involvement of Lipopolysaccharide-Binding Protein, CD14, and Bactericidal/Permeability-increasing Factor" *Infection and Immunity* 65(1):89-94.

Khan S. et al. 2010 "Synergistic Activity of OligoG with Anti-Gram-Negative Antibiotics against *Pseudomonas aeruginosa* and *Burkholderia* spp." Poster No. F1-1601 at ICAAC, Boston, Sep. 12-15, 2010.

Khan S. et al. 2010 "Effect of OligoG on Disruption of *Acinetobacter baumannii* Biofilms and Overcoming Multi-Drug Resistance" Poster No. F1-1602 at ICAAC, Boston, Sep. 12-15, 2010.

Khan S. et al. 2010 "Activity of OligoG Alginate Against Gram-Positive Bacteria, Alone and in Combination with Anti-Gram Positive Antibiotics" Poster No. F1-1600 at ICAAC, Boston, Sep. 12-15, 2010.

Khan, S. et al. 2011 "The Antimicrobial Effect of Alginate Oligosaccharides for the Treatment of Multi-Drug Resistant Bacterial Infections may be due to Cell Wall Disruption?" Poster No. F1-154 at ICAAC, Chicago, Sep. 17-20, 2011.

Kitamikado, M. et al 1992 "Two Types of Bacterial Alginate Lyases" *Appl Environ Microbiol* 58(8):2474-2478.

(56) References Cited

OTHER PUBLICATIONS

Kitamikado, M. et al. 1993 "Bacteriostatic Action of Oligosaccharides Prepared from Alginate by Enzymatic Degradation" *Nippon Suisan Gakkaishi—Bulletin of the Japanese Society of Scientific Fisheries* 59: 315-320.

Lasa, I. 2006 "Towards the identification of the common features of bacterial biofilm development" *International Microbiology*, 9:21-28.

McGowan, J.E. Jr. 2006 "Resistance in nonfermenting gram-negative bacteria: multidrug resistance to the maximum" *Am J Infection Control* 34: S29-S37.

Moore, J.E. et al. 2001 "Antibiotic resistance in *Burkholderia cepacia* at two regional cystic fibrosis centres in Northern Ireland: is there a need for synergy testing?" *J Antimicrobial Chemotherapy* 48: 319-321.

Moskowitz, S.M. et al. 2004 "Clinically Feasible Biofilm Susceptibility Assay for Isolates of *Pseudomonas aeruginosa* from Patients with Cystic Fibrosis" *Journal of Clinical Microbiology* 42(5): 1915-1922.

Mrsny R.J., et al. 1994 "Addition of a Bacterial Alginate Lyase to Purulent CF Sputum In Vitro Can Result in the Disruption of Alginate and Modification of Sputum Viscoelasticity" *Pulmonary Pharmacology*, 7:357-366.

Murata, K et al. 1992 "Continuous Depolymerization of Alginates by a Non-Support Bioreactor System Containing Flocculated Bacterial Cells" *Journal of Fermentation and Bioengineering* 73(2):172-174.

Otterlei, M et al. 1991 Induction fo Cytokine Production from Human Monocytes Stimulated with Alginate *Journal of Immunotherapy*, 10:286-291.

Powell, L. et al. 2012 "The Effects of the Alginate Oligosaccharide Oligo-G on the Surface and Rheological Properties of Gram-Negative Bacterial Biofilms using Atomic Force Microscopy" Poster at European Cystic Fibrosis Conference, Jun. 11, 2012.

Qiu, D, et al. 2007 "Regulated proteolysis controls mucoid conversion in *Pseudomonas aeruginosa*" *Proc Natl Acad Sci USA* 104(19):8107-8112.

Remminghorst, U. et al. 2006 "Bacterial alginates: from biosynthesis to applications" *Biotechnology Letters* 28:1701-1712.

Sletta, H. et al. 2011 "The Ability of Novel Alginate Oligosaccharides to Impair Fungal Adherence, Biofilm Formation and Potentiate Conventional Anti-Fungal Therapy in vitro" Poster No. F1-155 at ICAA, Chicago, Sep. 17-20, 2011.

Strugala et al. 2004, "Bioactive Properties of Epimerised Alginates" *Gums and Stabilisers for the Food Industry* 12:84-94.

Tang, J. X. et al. 2005 "Anionic poly(amino acid)s dissolve F-actin and DNA bundles, enhance DNase activity, and reduce the viscosity of cystic fibrosis sputum" *American Journal of Physiology—Lung, Cellular and Molecular Physiology* 289: L599-L605.

Thibault, F.M. et al. 2004 "Antibiotic susceptibility of 65 isolates of *Burkholderia pseudomallei* and *Burkholderia mallei* to 35 antimicrobial agents" *J Antimicrobial Chemotherapy* 54: 1134-1138.

Venes et al. 2001 "Taber's Cyclopedic Medical Dictionary", $19^{th}$ Edition, F.A. Davis Co., Philadelphia, PA, see p. 245, col. 1 ("biofilm") and see p. 1670, col. 2 ("plankton").

Venes et al. 2009 "Taber's Cyclopedic Medical Dictionary", $21^{st}$ Edition, F.A. Davis Co., Philadelphia, PA, see p. 264, col. 2 ("biofilm").

Ying, Q-L et al. 1996 "Alginate, the Slime Exopolysaccharide of *Pseudomonas aeruginosa*, Binds Human Leukocyte Elastase, Retards Inhibition by α-Proteinase Inhibitor, and Accelerates Inhibition by Secretory Leukoprotease Inhibitor" American *Journal of Respiratory Cell and Molecular Biology*, 15:283-291.

Yu, H. et al. 2002 "Persistent Infections and Immunity in Cystic Fibrosis" *Frontiers in Bioscience* 7:d442-457.

Ertesvåg, H. 2015 "Alginate-modifying enzymes: biological roles and biotechnological uses" *Frontiers in Microbiology*, vol. 6, Article 523 (in 10 pages).

Zhang, Z. et al. 2004 "Preparation and structure elucidation of alginate oligosaccharides degraded by alginate lyase from *Vibro* sp. 510" *Carbohydrate Research* 339: 1475-1481.

* cited by examiner

US 9,877,983 B2

USE OF ALGINATE OLIGOMERS IN COMBATING BIOFILMS

FIELD OF THE INVENTION

The present invention relates to a method of combating biofilms. In particular the present invention relates to the use of a particular class of alginates, and in particular certain alginate oligomers, to combat biofilms, including both on biotic and abiotic surfaces. Thus, both medical and non-medical uses and methods are provided, to combat biofilm infection or to combat biofilm formation on inanimate surfaces e.g. for disinfection and cleaning purposes. The invention is based on the surprising discovery that certain alginate oligomers are able to interact with and interfere with the biofilm.

BACKGROUND OF THE INVENTION

In general terms a biofilm is a collection, or community, of microorganisms surrounded by a matrix of extracellular polymers (also known in the art as a glycocalyx). These extracellular polymers are typically polysaccharides, notably polysaccharides produced by the organisms themselves, but they can contain other biopolymers as well. A biofilm will typically be attached to a surface, which may be inert or living, but it has also been observed that biofilms may form from microorganisms attached to each other or at any interface. Generally, therefore, a biofilm is characterised as a highly organised multicellular community of microorganisms encased in, or surrounded by, an extracellular polymer matrix, generally a polysaccharide matrix, and generally in close association with a surface or interface. Such a mode of growth is protective to the microorganisms, and renders them difficult to remove or eradicate (for example, as discussed further below, recalcitrant or resistant to anti-microbial agents or host defence or clearance mechanisms). It is believed, according to the present invention, that alginate oligomers may interact with the polymer matrix of the biofilm, and thus weaken the biofilm. As discussed further below, biofilms cause significant commercial, industrial and medical problems, in terms of infections. contamination, fouling and spoilage etc, and thus the present invention provides a significant advantage in enabling or facilitating the combating of such biofilms, including both reducing or preventing their formation, and rendering them more susceptible to removal or reduction, e.g. more susceptible to the effect of anti-microbial agents (including disinfectants or antibiotics) or indeed in the case of an infection, to the immune response of the infected host. The efficacy of anti-microbial agents, both therapeutic and non-therapeutic and including particularly antibiotics, may thus be enhanced.

Biofilms are found ubiquitously on a wide variety of surfaces or interfaces (e.g. water/solid and water/gas (for example water/air) interfaces) if conditions conducive to microbial colonisation exist. Basically a biofilm will form wherever there are microorganisms and an interface or surface, particularly a surface exposed to water or moisture and biofilms are now recognised as the natural state of microbial growth on such surfaces or interfaces. In basic terms, as noted above, a biofilm is the complex and organised arrangement of microbial colonies on a surface, or at an interface, which may occur particularly in the presence of water or moisture. The organisation of these colonies results from the ability of microorganisms to produce an organised extracellular matrix in which the cells are "embedded". This matrix is formed from biopolymers produced by the microorganisms with polysaccharides typically the predominant polymer.

The microorganisms in a biofilm community display properties at the cellular level (phenotype) that are not shared by their planktonic (free-floating) equivalents. In fact, it is believed that microorganisms in a biofilm are profoundly different from planktonic free-floating cells. Further differences can be also be observed at the community level and are attributed to the effects of the extracellular matrix. Perhaps most notable is the commonly observed phenomenon that microorganisms in a biofilm environment do not display the same susceptibilities to anti-microbial agents, e.g. antibiotics, anti-fungals and microbicides, and host immune defences or clearance mechanisms. It is thought that this resistance is due to the barrier effect of the extracellular matrix and/or a phenotypic change in the microbes themselves. For instance, once biofilms form, antibodies no longer attach to the microorganisms (e.g. bacteria) within the biofilm. Experiments have shown antibodies thickly crusted on the outside of biofilm, but not within the biofilm itself. Studies on white blood cell activity against biofilms have demonstrated similar findings. Toxin production might also different between a planktonic microbe and its equivalent residing in a biofilm colony suggesting phenotypic changes in the microbes. It is also believed that microorganisms in biofilms may grow more slowly, and as a result take up anti-microbial agents more slowly.

Biofilms form readily on aquatic environmental surfaces and an established microbial colony on any surface exposed to water (any "wet" surface) will almost certainly exist as a biofilm structure. Furthermore it is now becoming evident and increasingly documented that biofilms may also form in the case of microbial infections i.e. within or on an infected host. Thus biofilm formation may also occur on a "physiological" or "biological" surface, that is on an animate or biotic surface, or a surface on or in an infected host organism (e.g. a human or non-human animal subject), for example on an internal or external body or tissue surface. Such biofilm formation (or infection) on body tissues is increasingly believed to contribute to various infective diseases, including for example native valve endocarditis (mitral, aortic, tricupsid, pulmonic heart valves), acute otitis media (middle ear), chronic bacterial prostatitis (prostate), cystic fibrosis (lungs), pneumonia (respiratory tract), periodontitis (tissues supporting the teeth, e.g. gingiva, periodontal ligament, alvelor bone). Of course, both of these biofilm niches are present when medical devices are implanted and the formation of biofilm on such implanted ("in-dwelling") devices can lead to clinical problems with infection at such sites, such as prosthetic valve endocarditis and device-related infection, for example with intrauterine devices, contact lenses, prostheses (e.g. prosthetic joints) and at catheterisation sites, for example with central venous or urinary catheters.

A significant problem and risk with such biofilm infections is that microorganisms (or more particularly microcolonies) may break off or detach from the biofilm, and enter other tissues, including significantly the circulation. Such circulating biofilm-derived microorganisms can cause further infections and lead to significant clinical problems, particularly as the detached circulating microorganisms may have all the resistance characteristics of the parent community.

A biofilm infection typically develops gradually and may be slow to produce overt symptoms. Once established, however, biofilms are as noted above difficult to clear and a biofilm infection will typically be persistent, and rarely resolved by host defence or immune mechanisms, even in individuals with healthy innate and adaptive immune responses. Active host responses may indeed be detrimental, for example cell-mediated immunity (e.g. invading neutrophils) may cause collateral damage to neighbouring healthy host tissue. Biofilm infections respond only transiently to antibiotic therapy. Thus, whilst planktonic microbial cells may be cleared by antibodies or phagocytes, and are susceptible to anti-microbials, the microorganisms in biofilms tend to be resistant to antibodies, phagocytes and anti-microbials. Phagocytes are attracted to the biofilm, but phagocytosis is frustrated. Phagocytic enzymes are nonetheless released and may damage tissue around the biofilm. Planktonic bacteria may be released from the biofilm and such release may cause dissemination and acute infection in neighbouring tissue.

Body or tissue surfaces which are dead or damaged (e.g. necrotic or inflamed) are particularly susceptible to biofilm infection. Wounds are susceptible to infection and biofilm formation can occur in wounds that do not heal in a short amount of time. Wounds are an ideal environment for the formation of biofilms due to their susceptibility to bacterial colonisation and the availability of substrate and surface for biofilm attachment. Problematically, infection of a wound often delays healing further and thus renders that wound more susceptible to biofilm formation and established infection. Wounds in which healing is delayed (so called chronic wounds) represent sites of particular concern with respect to biofilm formation. A chronic wound is in an inflammatory state, with elevated levels of pro-inflammatory cytokines. The effect of these cytokines is to produce a swarming of the area with immune cells (neutrophils and macrophages). If this defence system is in any way delayed (as in chronic wounds), bacteria or other microorganisms have time to attach to the surface and enter the biofilm mode of growth. Evidence is increasingly growing that both chronic and acute wounds may be sites of biofilm infection, with evidence of diverse microbial communities or populations in wounds, particularly chronic wounds, including anaerobic bacteria within chronic wounds. Chronic wound infections share two important attributes with other biofilm infections: persistent infection that is not cleared by the host immune system even in individuals with healthy innate and adaptive immune reactions, and increased resistance to systemic and topical antimicrobial agents. Accordingly, biofilm based infection is very difficult to treat and biofilm contamination is very difficult to eradicate. Frequent debridement is one of the most clinically effective treatments to help heal chronic wounds. This is an effective treatment, in part, because it physically removes the biofilm from the wound. This is similar in principle to resolving infections from biofilm-colonized in-dwelling medical devices (e.g. catheters)—where antibiotic therapy is ineffective the most effective approach is to remove or replace the biofilm-infected device.

Chronic wounds are a major health problem throughout the world and represent a significant drain on clinical resources. Three principle types of chronic wound are diabetic foot ulcers, venous leg ulcers and pressure ulcers, although other wounds, including surgical wounds, may become chronic. The care of such wound imposes enormous material and patient costs, and hence an effective anti-biofilm treatment, or indeed any treatment which assisted in or facilitated the treatment of biofilms, and thus accelerated or facilitated wound healing, would be of very significant impact.

More generally, given the widespread occurrence of biofilms and the medical, environmental, industrial or other commercial problems they cause, any means of improving or enabling the combating of biofilms would be very important, both clinically and commercially.

SUMMARY OF THE INVENTION

A need therefore exists for new methods of combating biofilms, both in clinical and industrial or commercial situations, and the present invention is directed to addressing this need.

In particular, and as noted above, it has been found that a particular class of alginates, namely certain alginate oligomers, are effective as anti-biofilm agents. The alginate oligomers may interact with the extracellular polymers of the biofilm, and thereby weaken it, enabling or facilitating its removal or breakdown (or disruption), and/or facilitating the access of anti-microbial agents to the biofilm, thereby enhancing their efficacy against the biofilm. Accordingly, according to the present invention there is proposed a new method or means for combating biofilm involving the use of alginate oligomers.

Alginates are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea*, *Lessonia* and *Laminaria*) and bacteria such as *Pseudomonas aeruginosa* and *Azotobacter vinelandii*. Other pseudomonads (e.g. *Pseudomonas fluorescens*, *Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185(12) 3515-3523 and WO 2004/011628).

Alginates are typically isolated from natural sources as large high molecular weight polymers (e.g. an average molecular weight in the range 300,000 to 500,000 Daltons. It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (i.e. such alginates are still considered to be large polymers) although alginates of an average molecular weight of approximately 35,000 Daltons have been used in pharmaceuticals.

It has now been found that alginate oligomers have the ability to interfere with the extracellular matrix of biofilms. Without wishing to be bound by any particular theory, this interference is believed to cause the extracellular matrix of the biofilm to break down and this thus leads to the physical disruption of the biofilm. The breakdown also increases the exposure of the microorganisms within the biofilm (or their immunogenic components, e.g. LPS and peptideoglycan structures) to the immune defences of an infected host and/or any antimicrobial agents that have been, or will be, applied. The breakdown also reduces the intimacy of the relationship between the extracellular matrix and the microorganisms and this leads to an increase in the sensitivity of the microorganism to anti-microbial agents at a phenotypic level.

DETAILED DESCRIPTION OF THE PREFERRED EMBODIMENT

Figure 1:
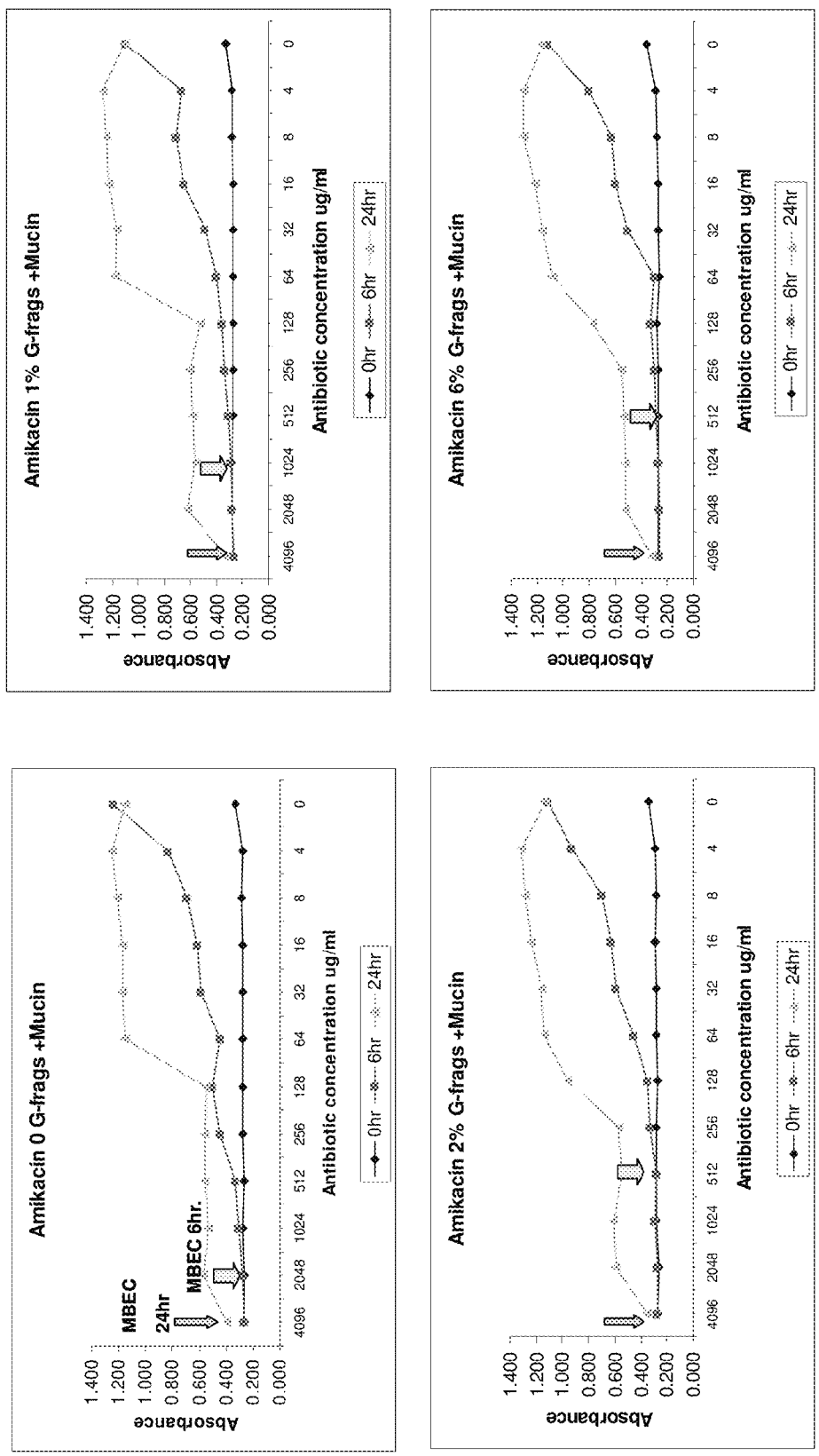
FIG. 1 shows bacterial growth in *Pseudomonas* biofilms, generated overnight and then treated with mucin (2.5 g/L) and G-fragments (0, 1%, 2% or 6%) overnight, at 0 hr, 6 hr and 24 hr after overnight treatment with amikacin (4096-0 µg/ml).

The invention therefore provides a method for combating biofilm, said method comprising contacting said biofilm with an alginate oligomer.

As noted above, alginates typically occur as polymers of an average molecular weight of at least 35,000 Daltons i.e. approximately 175 to 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than 175 monomer residues), in particular an alginate of an average molecular weight of less than 30,000 Daltons (i.e. less than approximately 175 or less than 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, preferably 2 to 75, preferably 2 to 50, more preferably 2 to 40, 2 to 35 or 2 to 30, i.e. an alginate oligomer for use according to the invention will typically have an average molecular weight of 350 to 20,000 Daltons, preferably 350 to 15,000 Daltons, preferably 350 to 10,000 Daltons and more preferably 350 to 8000 Daltons, 350 to 7000 Daltons, or 350 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35 or 2 to 30.

As noted above, biofilms typically form on surfaces or interfaces and the biofilm which is treated according to the present invention may be on any surface or interface. Accordingly, in the method of the invention the biofilm may be on any animate or inanimate (or biotic or abiotic), surface i.e. any living surface, or surface derived from living material (e.g. dead or damaged tissue e.g. necrotic tissue) (the term "animate" is used herein to include any living surface or any surface derived from living material, in particular a living surface which has died), or any inert or non-living surface (a surface which has not previously been alive or animate).

The term "contacting" encompasses any means of delivering the alginate oligomer to the biofilm, whether directly or indirectly, and thus any means of applying the alginate oligomer to the biofilm or exposing the biofilm to the alginate oligomer e.g. applying the alginate oligomer directly to the biofilm, or administering the alginate oligomer to a subject with a biofilm infection. It will be appreciated therefore that both in vitro and in vivo methods are included.

More particularly the biofilm will be contacted with an effective amount of the alginate oligomer, more particularly an amount of the alginate oligomer effective to combat biofilm.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 60%, more particularly at least 70% or 75%, even more particularly at least 80, 85, 95 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90 or 95% of the single G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5 to 18 or 7 to 15 or 8 to 12, especially 10.

The molecular weight distribution is preferably such that no more than 5% mole has a DP of two higher than the relevant upper limit for $DP_n$. Likewise it is preferred that no more than 5% mole has a DP below a number two smaller than the relevant lower limit for $DP_n$. Suitable alginate oligomers are described in WO2007/039754, WO2007/039760, and WO 2008/125828, the disclosures of which are explicitly incorporated by reference herein in their entirety.

Representative suitable alginate oligomers have a $DP_n$ in the range 5 to 30, a guluronate/galacturonate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate/galacturonate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate/galacturonate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate/galacturonate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate/galacturonate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate/galacturonate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate/galacturonate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate/galacturonate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate/galacturonate fraction ($F_G$) of at least 0.92, a mannuronate fraction ($F_M$) of no more than 0.08, and having at least 95% mole with a degree of polymerization less than 17.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived, from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describes a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from but not limited to *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*, although algal sources are expected to be most suitable on account of the fact that the alginates produced in these organisms tend to have primary structures in which the majority of the G residues are arranged in G-blocks rather than as single residues.

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an alginate source material) can be increased by epimerisation, for example with mannuran C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvåg et al (supra) and Strugala et al (Gums and Stabilisers for the Food Industry, 2004, 12, The Royal Society of Chemistry, 84-94). Epimerisation with one or more *Azotobacter vinelandii* AlgE epimerases other than AlgE$_4$ is preferred as these enzymes are capable of producing G block structures. Mutated versions or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure of alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra). The skilled man would be able to use this teaching to produce new mutants that would produce alginate oligomers of the invention without undue burden.

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer can be influenced by the culture conditions.

It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in anti-biofilm activity that is substantially lower than that of the unmodified polymer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginates of the invention.

By "biofilm" it is meant a community of microorganisms characterized by a predominance of sessile cells that are attached to a substratum or interface or to each other,(some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts).

The term "combating biofilm" is used broadly herein to include any effect in disrupting, reducing, or breaking down a biofilm (i.e. "attacking" an existing biofilm) or of rendering it more susceptible to the effect of an anti-microbial agent or a host immune response, as well as inhibiting, reducing, delaying or preventing the formation of a biofilm. Thus "combating" includes any treatment of a biofilm which has negative effect on the biofilm.

"Combating biofilm" thus includes both preventative and reactionary measures or treatments. Combating biofilm therefore encompasses the prevention of formation of a biofilm, the elimination of a biofilm, a reduction in biofilm size, a reduction in the number of microbes in a biofilm colony, a reduction or cessation in the rate of growth of a biofilm, a reduction in or cessation of the rate of expansion in the number of microbes in a biofilm colony, a reduction in the physical integrity of a biofilm, an increase in the sensitivity of the microbes in a biofilm colony to an anti-microbial agent or host immune defence mechanism and an increase in the permeability of a biofilm to an anti-microbial agent or host immune defence mechanism.

The method of the invention may thus be used clinically, e.g. in the treatment of a biofilm infection, or it may be used in the cleaning or decontamination of any surface, e.g. of a commercial or industrial surface.

The size, structure, integrity, and number of microorganisms in a biofilm can be analysed by any convenient method. For instance, scanning and transmission electronic microscopy is often used to assess the size, integrity and structure of a biofilm. Histochemical staining of the microorganisms and/or the extracellular matrix components is also routine (e.g. BODIPY™ 630/650-X SE dye for matrix components from *Pseudomonas* biofilms and FM™ 1-43 dye for *Pseudomonas* cell membranes) and can be used to assess microbe numbers and biofilm structure and integrity visually or with assistance with cell sorting devices, confocal microscopes or epifluorescence microscopes. The MBEC assay, Moskowitz S M, et al (2004) J Clin Microbiol, 42: 1915-1922 and described in more detail in the Examples may be used to assess the sensitivity of microorganisms in a biofilm to an anti-microbial agent. Donlan and Costerton, 2002, Clin. Mic. Rev., Vol 15(2), 167-193 provides further examples.

The biofilms that may be combated in accordance with the invention are not limited in terms of the microorganisms in the biofilms as the alginate oligomer of the invention, inter alia, targets the extracellular matrix. Accordingly, the biofilm may comprise any class, genus or species of microorganism, namely any microorganism that may form a biofilm. Such microorganisms include typically bacteria, including any genus or species of bacteria. Thus, the bacteria may be gram positive or gram negative, or gram test non-responsive. They may be aerobic or anaerobic. The bacteria may be pathogenic or non-pathogenic, or spoilage or indicator bacteria. Examples of genera or species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, lgnavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia*, and *Yokenella*; e.g. gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphyloccocus aureus, Staphylococcus epidermidis, Staphylococcus aqui, Streptococcus pyogenes, Streptococcus agalactiae, Listeria monocytogenes, Listeria*

*ivanovii, Bacillus anthracis, B. subtilis, Nocardia asteroides, Actinomyces israelii, Propionibacterium acnes,* and *Enterococcus* species and Gram-negative bacteria such as *Clostridium tetani, Clostridium perfringens, Clostridium botulinum, Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella bumetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum, Cowdria ruminantium.*

Thus, by way of representative example, the biofilm may contain bacteria of the genus *Staphylococcus, Pseudomonas, Legionella, Mycobacterium, Proteus, Klebsiella, Fusobacterium* or other enteric or coliform bacteria.

Biofilms may also contain fungi, including for example from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidiodes brasiliensis, Blastomyces dermitidis, Pneomocystis camii, Penicillium mameffi, Alternaria alternate.*

Also contained in a biofilm may be algae and representative algal species include *Chaetophora, Chlorella protothecoides, Coleochaete scutata, Coleochaete soluta, Cyanidioschyzon merolae Aphanochaete, Gloeotaenium, Oedogonium, Oocystis, Oscillatoria, Paradoxia multisitia, Phormidium, Chroococcus, Aphanothece, Fragillaria, Cocconis, Navicula, Cymbella, Phaeodactylum* as well as cyanobacteria (blue-green algae) and diatoms such as *Nitzschia palea.*

Biofilms can also contain other organisms such as, for example, parasites, e.g. protozoa such as *Toxoplasma* species e.g. *Toxoplasma gondii, Plasmodium* species such as *Plasmodium falciparum, Plasmodium vivax, Plasmodium malariae. Trypanosoma brucei, Trypanosoma cruzi, Leishmania* species such as *Leishmania major, Schistosoma* such as *Schistosoma mansoni* and *Entamoeba histolytica.*

It is common for a biofilm to comprise a mixed colony of microorganisms and so the biofilm combated by the alginate oligomers according to the invention may comprise any number of the above-mentioned species. Preferably at least two, more preferably at least 5 and most preferably at least 10.

Preferably the biofilm colony comprises microbes from at least one of the following genera: *Citrobacter, Enterobacter, Escherichia, Hafnia, Serratia, Yersinia, Peptostreptococcus, Bacteriodes, Pseudomonas, Legionella, Staphylococcus, Enterococcus, Streptococcus, Klebsiella, Candida, Proteus, Burkholderia, Fusobacterium* and *Mycobacterium,* for instance, *Staphylococcus aureus, Staphylococcus epidermidis, Legionella pneumophila, Candida albicans, Pseudomonas aeruginosa, Burkholderia cepacia* and *Streptococcus Pyogenes.*

As noted above the biofilm may be present on a surface. The surface is not limited and includes any surface on which a microorganism may occur, particularly, as noted above, a surface exposed to water or moisture. The surface may be biotic or abiotic, and inanimate (or abiotic) surfaces include any such surface which may be exposed to microbial contact or contamination. Thus particularly included are surfaces on machinery, notably industrial machinery, or any surface exposed to an aquatic environment (e.g. marine equipment, or ships or boats or their parts or components), or any surface exposed to any part of the environment, e.g. pipes or on buildings. Such inanimate surfaces exposed to microbial contact or contamination include in particular any part of: food or drink processing, preparation, storage or dispensing machinery or equipment, air conditioning apparatus, industrial machinery, e.g. in chemical or biotechnological processing plants, storage tanks and medical or surgical equipment. Any apparatus or equipment for carrying or transporting or delivering materials, which may be exposed to water or moisture is susceptible to biofilm formation. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases. As noted above, medical or surgical equipment or devices represent a particular class of surface on which a biofilm may form. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

The surface can be made of any material. For example it may be metal, e.g. aluminium, steel, stainless steel, chrome, titanium, iron, alloys thereof, and the like. The surface can also be plastic, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. Other examples include acetal copolymer, polyphenylsulfone, polysulfone, polythermide, polycarbonate, polyetheretherketone, polyvinylidene fluoride, poly(methyl methacrylate) and poly(tetrafluoroethylene). The surface can also be brick, tile, ceramic, porcelain, wood, vinyl, linoleum, or carpet, combinations thereof, and the like. The surfaces can also be food, for example, beef, poultry, pork, vegetables, fruits, fish, shellfish, combinations thereof, and the like.

A biotic or animate surface may include any surface or interface in or on the body. It may as noted above accordingly be viewed as a "physiological" or "biological" surface. It may be any internal or external body surface, including of any tissue, which may include haematological or haemotopoeitic tissue (e.g. blood). As discussed above, dead or dying (e.g. necrotic) or damaged (e.g. inflamed or disrupted or broken) tissue is particularly susceptible to biofilm growth and such tissue is encompassed by the term "animate" or "biotic". The surface may be a mucosal or nonmucosal surface.

Representative biotic surfaces include, but are not limited to any surface in the oral cavity, e.g. teeth, gingiva, gingival crevice, periodontal pocket, reproductive tract (e.g. cervix, uterus, fallopian tubes), the peritoneum, middle ear, prostate, urinary tract, vascular intima, conjunctiva, corneal tissue, the respiratory tract, lung tissue (e.g. bronchial and alveolial), heart valves, gastrointestinal tract, skin, scalp, nails and the interior of wounds, particularly chronic wounds, which may be topical or internal wounds.

In one aspect the surface will not be mucosal, or more particularly will not have a hyperviscous mucus coating. The skilled person will be able to determine when the mucous at a given surface is hyperviscous. In one embodiment the surface will not be the surface of a mucous secreting tissue. More particularly in such an embodiment the surface will not be the surface of a mucous-coated tissue. The skilled person will know from his common general knowledge the tissues that secrete mucous and those that are mucous-coated.

It will accordingly be seen that the invention provides medical uses of the alginate oligomers as defined herein, for the treatment or prevention of a biofilm infection in a subject (e.g. biofilm infection with any microorganism, including bacteria, viruses, fungi or parasites such as protozoa). The infection may be a pathogen infection. Representative examples of microorganisms that can cause infection are described above. Infections caused by *Citrobacter, Enterobacter, Escherichia, Hafnia, Serratia, Yersinia, Peptostreptococcus, Bacteriodes, Pseudomonas, Legionella, Staphylococcus, Enterococcus, Streptococcus, Klebsiella, Candida, Proteus, Burkholderia, Fusobacterium* and *Mycobacterium*, for instance, *Staphylococcus aureus, Staphylococcus epidermidis, Legionella pneumophila, Candida albicans, Pseudomonas aeruginosa, Burkholderia cepacia* and *Streptococcus Pyogenes* are of note. Infections caused by and *Pseudomonas*, e.g. *Pseudomonas aeruginosa*, infections are of particular note.

The term "in a subject" is used broadly herein to include biofilm infection which occurs inside a subject or on a subject, e.g. on an external body surface. The biofilm infection may be chronic (i.e. may be a chronic biofilm infection), e.g. an infection that has persisted for at least 5 or at least 10 days, particularly at least 20 days, more particularly at least 30 days, most particularly at least 40 days. Chronic infections often manifest as biofilm infections, but a biofilm infection need not be a chronic infection as defined herein.

In this aspect of the invention the biofilm infection may occur on a surface in or on the subject (i.e. a biotic surface as discussed above) and/or a surface of a medical device, particularly an implantable or "in-dwelling" medical device.

Accordingly, in this aspect the invention provides an alginate oligomer (which may be any alginate oligomer as herein defined) for use in the treatment or prevention of a biofilm infection in a subject.

Alternatively put, this aspect of the invention provides the use of an alginate oligomer for the manufacture of a medicament for use in the treatment or prevention of a biofilm infection in a subject.

This aspect of the invention also provides a method for the treatment or prevention of a biofilm infection in a subject, said method comprising administering a pharmaceutically effective amount of an alginate oligomer to a subject in need thereof.

Also provided is the use of an alginate oligomer in the treatment or prevention of a biofilm infection in a subject.

The subject may be any human or non-human animal subject, but more particularly may be a vertebrate, for example a mammalian subject, an avian subject, a fish or a reptile. Human subjects are preferred, but the subject may be, for example, any livestock or domestic animal, or for example an animal in a zoo. Thus representative animals include dogs, cats, rabbits, mice, guinea pigs, hamsters, horses, pigs, sheep, goats, cows, birds and fish. Veterinary uses of the invention are thus covered. The subject may be viewed as a patient.

A biofilm infection can occur in any subject but some subjects will be more susceptible to infection that others. Subjects who are susceptible to biofilm infection include, but are not limited to, subjects whose epithelial and/or endothelial barrier is weakened or compromised, subjects whose secretion-based defences to microorganisms infection have been abrogated, disrupted, weakened or undermined, and subjects who are immunocompromised, immunodeficient or immunosuppressed (i.e. a subject in whom any part of the immune system is not working normally, or is working sub-normally, in other words in whom any part of the immune response, or an immune activity is reduced or impaired, whether due to disease or clinical intervention or other treatment, or in any way).

Representative examples of subjects who are susceptible to biofilm infection include, but are not limited to, subjects with a pre-established infection (e.g. with bacteria, viruses, fungi or parasites such as protozoa), especially subjects with HIV, subjects with sepsis and subjects with septic shock; subjects with immunodeficiency, e.g. subjects preparing for, undergoing or recovering from chemotherapy and/or radiotherapy, organ (e.g. bone marrow, liver, lung, heart, heart valve, kidney, etc.) transplant subjects (including autograft, allograft and xenograft patients), subjects with AIDS; subjects resident in a healthcare institution, e.g. hospital, especially subjects in intensive care or critical care (i.e. those units concerned with the provision of life support or organ support systems to patients); subjects suffering from trauma; subjects with burns, subjects with acute and/or chronic wounds; neonatal subjects; elderly subjects; subjects with cancer (defined broadly herein to include any neoplastic condition; malignant or non-malignant), especially those with cancers of the immune system (e.g. leukaemias, lymphomas and other haematological cancers); subjects suffering from auto-immune conditions such as rheumatoid arthritis, diabetes mellitus type I, Crohn's disease, especially those undergoing immunosuppression treatment for those diseases; subjects with reduced or abrogated epithelial or endothelial secretion (e.g. mucous, tears, saliva) and/or secretion clearance (e.g. subjects with poorly functioning cilia on mucosal tissue and/or patients with hyperviscous mucous (e.g. smokers and subjects with COPD, bronchitis, cystic fibrous, emphysema, lung cancer, asthma, pneumonia or sinusitis) and subjects fitted with a medical device.

Thus, subjects in whom biofilm infections may particularly be combated according to the present invention include patients who remain impaired, whether due to poor perfusion, repetitive trauma, poor nutrition, poor oxygenation or white cell dysfunction.

Of particular note are subjects that have undergone physical trauma. The trauma itself might cause a weakening in or compromisation of an epithelial and/or endothelial barrier of the subject or the subject may become immunocompromised in response to the trauma (a shock response). The term "trauma" refers broadly to cellular attack by foreign bodies and/or physical injury of cells. Included among foreign bodies are microorganisms, particulate matter, chemical agents, and the like. Included among physical injuries are mechanical injuries; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Also of particular note are subjects that have a burn. Any burn, in particular a severe burn, has a significant impact on the integrity of the epithelial and/or endothelial barrier of the subject and the subject will often become immunocompromised in response to the burn (a shock response).

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

Epidermal burn severity is commonly classified in two ways. Most common is the classification by degree. First-degree burns are usually limited to erythema (redness) in the general area of the injury and a white plaque at the site of injury. The cellular trauma of these burns extends only as deep as the epidermis. Second-degree burns also display erythema in the general area of the injury but with superficial blistering of the epidermis. The cellular trauma of second-degree burns involves the superficial (papillary) dermis and may also involve the deep (reticular) dermis layer. Third-degree burns are those in which the epidermis is lost with damage to the hypodermis. Damage is typically extreme including charring. Sometimes eschar, (dry, black necrotic tissue) will be present. Third-degree burns may require grafting. In fourth-degree burns catastrophic damage of the hypodermis occurs, e.g. the hypodermis is completed lost, with damage extending to the underlying muscle, tendon, and ligament tissue. Charring and eschar are observed. Grafting is required if the burn does not prove to be fatal.

Another common classification system is the classification by thickness. "Superficial thickness" burns correspond to first degree burns. The spectrum of second degree burns is covered by two classes of "partial thickness" burns. "Partial thickness-superficial" are burns that affect the epidermis only as far as the papillary dermis. "Partial thickness-deep" are burns that affect the dermis as far as the reticular dermis. "Full thickness" burns correspond to third and fourth degree burns.

Some physical injuries, e.g. some burns, and cellular attacks by foreign bodies result in the formation of a wound. More specifically a wound may be considered to be a breach in, or denudement of, a tissue. Wounds may also be caused by a spontaneously forming lesion such as a skin ulcer (e.g. a venous, diabetic or pressure ulcer), an anal fissure or a mouth ulcer.

Wounds are typically defined as either acute or chronic. Acute wounds are wounds that proceed orderly through the three recognised stages of the healing process (i.e. the inflammatory stage, the proliferative stage and the remodelling phase) without a protracted timecourse. Chronic wounds, however, are those wounds that do not complete the ordered sequence of biochemical events of the healing process because the wound has stalled in one of the healing stages. Commonly, chronic wounds are stalled in the inflammatory phase. In accordance with a particular aspect of the present invention, a chronic wound is a wound that has not healed within at least 40 days, particularly at least 50 days, more particularly at least 60 days, most particularly at least 70 days.

As discussed above, wounds are an ideal environment for infection, including biofilm infection, and particularly chronic biofilm infection, due to their lack of an epithelial barrier and the availability of substrate and surface for colonisation and biofilm attachment. Problematically, infection of a wound often delays healing further and thus renders that wound more susceptible to biofilm formation and established infection. The alginates of the invention are therefore effective in the treatment and prevention of biofilm infection of wounds and the treatment of chronic wounds represents one preferred aspect of the present invention.

Therefore, in an embodiment of the invention there is provided a method for the treatment or prevention of biofilm infection, particularly chronic biofilm infection in above-mentioned subjects, in particular in subjects with respiratory diseases or disorders e.g. cystic fibrosis, wounds, burns and/or traumas, said method comprising administering a pharmaceutically effective amount of an alginate oligomer as defined herein to the subject.

In an aspect of particular importance, the alginate oligomers may be used to treat or prevent biofilm infection in wounds, e.g. burns, for example in the treatment of infected wounds, e.g. burns.

Through the ability to treat and prevent biofilm infection of wounds the alginate oligomers defined herein can remove one of the obstacles to wound healing and therefore the alginate oligomers defined above are also effective in the promotion of healing of acute and chronic wounds.

By promotion of healing it is meant that the treatment accelerates the healing process of the wound in question (i.e. the progression of the wound through the three recognised stages of the healing process). The acceleration of the healing process may manifest as an increase in the rate of progression through one, two or all of the healing stages (i.e. the inflammatory stage, the proliferative stage and/or the remodelling phase). If the wound is a chronic wound that is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal.

The alginate oligomers may be used to treat biofilm infections wherever they may occur in or on the body. Thus, in another embodiment, the biofilm infection may be an infection of a medical device, particularly an in-dwelling medical device.

As noted above, biofilms occur on teeth, for example in the form of dental plaque. The alginate oligomers may be used according to the present invention as oral healthcare agents, for example in the control of dental plaque, e.g. to remove it, or reduce it or to prevent, reduce or delay its development. They may also be used in the treatment and prevention of infections or infectious disease which may occur in the oral cavity, for example gingivitis and periodontitis Whilst as noted above the treatment of biofilm infections of the lungs and respiratory tract and all areas of the body is generally covered by the present invention, in one embodiment, the medical uses of the invention are not directed to the treatment of (i) biofilms in the respiratory tract of patients suffering from COPD's (chronic obstructive pulmonary diseases), in particular the sinuses and the lungs, in particular in the treatment of cystic fibrosis, chronic obstructive pulmonary disease, emphysema, bronchitis and sinusitis; (ii) in the middle ear of patients suffering from glue ear; or (iii) in the reproductive tract of female patients with impaired fertility; or (iv) in the digestive tract of patients with digestive tract malfunction (e.g. constipation).

In specific embodiments of the invention the alginate oligomers may be used in the treatment of native valve endocarditis, acute otitis media, chronic bacterial prostatitis, pneumonia, dental plaque, periodontitis, biofilm infections in respiratory diseases, which may include cystic fibrosis and asthma, and device related infection associated with implantable or prosthetic medical devices e.g. prosthetic valve endocarditis or infection of lines or catheters or artificial joints or tissue replacements.

A "pharmaceutically effective" amount of the alginate is the amount of alginate that provides a measurable effect on the targeted biofilm (as defined above) and/or a measurable effect on the condition being targeted. This amount can be determined with reference to standard practices for deciding dosage amounts and the skilled man will be able to detect evidence of successful treatment from his experience and with the aid of routine tests available to him that are designed to monitor biofilm size, structure, integrity and colony number (for instance those described above) and tests designed to monitor the targeted condition.

Suitable doses of alginate will vary from subject to subject and can be determined by the physician or veterinary practitioner in accordance with the weight, age and sex of the subject, the severity of the condition, the mode of administration and also the particular alginate oligomer selected. Typically the alginate oligomers of the invention will be applied to the biofilm at a local concentration of up to 10%, preferably up to 6%, more preferably up to 4% and most preferably up to 2%.

Treatment" when used in relation to biofilm infection (i.e. in relation to the treatment of a medical condition/infection in a subject as opposed to when used in relation to the biofilm itself) is used broadly herein to include any therapeutic effect, i.e. any beneficial effect on the condition or in relation to the biofilm infection. Thus not only included is eradication or elimination of the infection, or cure of the subject or infection, but also an improvement in the infection or condition of the subject. Thus included for example, is an improvement in any symptom or sign of the infection, or in any clinically accepted indicator of the infection/condition (for example a decrease in wound size or an acceleration of healing time). Treatment thus includes both curative and palliative therapy, e.g. of a pre-existing or diagnosed infection/condition, i.e. a reactionary treatment.

"Prevention" as used herein refers to any prophylactic effect. It thus includes delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom.

Specifically, the alginates of the invention can be taken as a prophylactic treatment, for example to prevent, or at least minimise the risk, of biofilm infection (e.g. by a pathogen). This aspect of the invention is of particular utility in the care of hospitalised patients as the risk of contracting a nosocomial infection (commonly known as hospital related/acquired infection or healthcare-associated infection), e.g. *Staphylococcus aureus*, Methicillin Resistant *Staphylococcus aureus* (MRSA), *Pseudomonas aeruginosa, Acinetobacter baumannii, Stenotrophomonas maltophilia, Clostridium difficile, Mycobacterium tuberculosis* and Vancomycin-Resistant *Enterococcus*, can be minimised with a prophylactic regime of the alginate oligomers defined herein. This aspect of the invention is also of particular utility in the care of subjects suffering from trauma, subjects with a burn and subjects with wounds, all of which, as discussed above, are more susceptible to pathogen infection than a subject that is not affected similarly.

Generally, subjects in need of treatment or prophylaxis according to the invention will be diagnosed as suffering or at risk from the target condition, or identified as having or at risk of developing a biofilm infection.

Specifically, the alginate oligomers of the invention can be taken as a prophylactic treatment to prevent, or at least minimise the risk, of developing a biofilm infection, including for example the infection of wounds, native valve endocarditis, acute otitis media, chronic bacterial prostatitis, periodontitis, infections of the respiratory tract and lungs (e.g. cystic fibrosis or other respiratory diseases, dental plaque, pneumonia, or infection of a medical (e.g. indwelling) medical device.

In one advantageous embodiment of the invention the alginate oligomers may be used in conjunction or combination with an anti-microbial agent. In the context of a medical use, such an agent may be any clinically-useful anti-microbial agent and particularly an antibiotic. In the context of non-clinical uses, the anti-microbial agent may again be any anti-microbial agent used for such purposes, e.g. any disinfectant or antiseptic or cleaning or sterilising agent. The agents may be used separately, or together in the same composition, simultaneously or sequentially or separately, e.g. at any desired time interval.

Thus by way of representative example, the anti-microbial agent may be used after the alginate oligomer, but a preceding or simultaneous use may be beneficial in some circumstances.

Any anti-microbial agent that targets at least one of microorganisms in the target biofilm may be used. The choice of anti-microbial agent will of course need to be appropriate for the surface undergoing treatment, but for instance anti-microbial agents, e.g. antibiotics, anti-fungals, antiseptics may be used and/or sterilising conditions such as irradiation (e.g. UV, X-ray, gamma) extremes of temperature, and extremes of pH.

Representative antibiotics include, but are not limited to the aminoglycosides (e.g. amikacin, gentamicin, kanamycin, neomycin, netilmicin, streptomycin, tobramycin); the carbecephems (e.g. loracarbef); the 1st generation cephalosporins (eg cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, t roleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the carbapenems (e.g. imipenem, meropenem, ertapenem, doripenem, panipenem/betamipron, biapenem, PZ-601); chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin. The antibiotics vancomycin, tobramycin, meropenem, ciprofloxacin, piperacillin, colistin, aztreonam, ciprofloxacin and azithromycin are preferred.

Representative antiseptics include, but are not limited to chlorine bleach (sodium hypochlorite), quaternary ammonium compounds (e.g. benzalkonium chloride, cetyl trimethylammonium bromide, cetylpyridinium chloride), hydrogen peroxide, phenol compounds (e.g. TCP), alcohols (e.g. ethanol), Virkon™, iodine compounds (e.g. povidone-iodine), silver compounds (e.g. elemental silver nano/microparticles).

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

The anti-microbial agent may conveniently be applied before, simultaneously with or following the alginate. Conveniently the anti-microbial agent is applied at substantially the same time as the alginate or afterwards. For example, the anti-microbial agent is applied at least 1 hour, preferably at least 3 hours, more preferably at least 5 and most preferably at least 6 hours after the alginate oligomer is administered. To optimise the anti-microbial effect of the anti-microbial agent the antimicrobial agent can be given (e.g. administered or delivered) repeatedly at time points appropriate for the agent used. The skilled person is be able to devise a suitable dosage or usage regimen. In long term treatments the alginate can also be used repeatedly. This can be as frequently as the anti-microbial agent, but will typically be less frequently. The frequency required will depend on the location of the biofilm infection, colony composition and the anti-microbial used and the skilled person is able to optimise the dosage or usage patterns to optimise results In an advantageous embodiment the anti-microbial agent may be used or applied after physical removal or reduction (e.g. debridement) of the biofilm from the surface.

Following removal of, or an attempt to remove, the biofilm, the surface may be contacted with the alginate oligomers for between 0 and 24 hours, particularly 2 and 12 hours, more particularly 4 and 8 hours, most particularly 5 and 7 hours, e.g. 6 hours. Following this, an anti-microbial agent may if desired be applied. Such a scenario may be desirable or particularly applicable in a clinical setting. In the case of biofilm infected wounds the duration of incubation can be conveniently be designed to correspond to scheduled changes of the wound dressing.

Physical removal of the biofilm can be carried out with any suitable surgical, mechanical or chemical means. Conveniently this can be the use of a liquid, gel, gel-sol, semi-solid compositions or gas applied at pressure to the biofilm, sonication, laser, or by abrasive implement. A composition used in the removal itself or as a wash solution before, during or afterwards may conveniently contain the alginate oligomer.

Accordingly, in one specific embodiment is provided a debridement or wash composition e.g. solution for wounds containing an alginate oligomer, particularly any alginate oligomer as herein defined. Such a debridement composition will typically be a sterile solution, particularly an aqueous sterile solution or an oil-based sterile solution, and may additionally contain proteolytic enzymes (e.g. collagenase, trypsin, pepsin, elastase), an abrasive solid phase (e.g. colloidal silica, ground pumice, ground plant or animal shell).

Use in combination or conjunction with other biofilm disrupting agents may be beneficial. Biofilm disruptors include, but are not limited to proteases, e.g. serine proteases, metalloproteases and cysteine proteases (examples of these types of proteases are listed in EP0590746, the entire contents of which are incorporated herein by reference); nucleases, e.g. DNase I and II, RNase A, H, I, II, III, P, PhyM, R; lipases and enzymes capable of degrading polysaccharides, gelsolin, a thiol reducing agent, an acetylcysteine, an uncharged low molecular weight polysaccharide (e.g. dextran), or an anionic polyamino acid (e.g. poly ASP or poly GLU).

Particular mention may be made of alginate lyase, and the combined use of this with an alginate oligomer as defined herein represents one possible specific embodiment of this aspect of the invention.

Use in combination or conjunction with immunostimulatory agents may also be beneficial in the treatment of biofilms in a clinical situation. These immunostimulatory agents may conveniently be used at timepoints corresponding to those described above in relation to anti-microbial agents and may optionally be used in combination with an alginate oligomer and an anti-microbial agent Suitable immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

Use of the alginate oligomers in combination or conjunction with growth factors, e.g. PDGF, FGF, EGF, TGF, hGF and enzymes may also be beneficial in the medical uses of the invention. Representative examples of suitable enzymes include but are not limited to proteases, e.g. serine proteases, metalloproteases and cysteine proteases (examples of these types of proteases are listed in EP0590746, the entire contents of which are incorporated herein by reference); nucleases, e.g. DNase I and II, RNase A, H, I, II, III, P, PhyM, R; lipases and enzymes capable of degrading polysaccharides.

Use of the alginate oligomers in combination or conjunction with a physiologically tolerable mucosal viscosity reducing agent could also be beneficial, e.g. a nucleic acid cleaving enzyme (e.g. a DNase such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). Ambroxol, romhexine, carbocisteine, domiodol, eprazinone, erdosteine, letosteine, mesna, neltenexine, sobrerol, stepronin, tiopronin are specific mucolytics of note. The use of a DNase is especially preferred.

As discussed above, the alginate oligomers may be used optionally with any other therapeutically active agent it may be desired to use, e.g. an anti-inflammatory agent. The combined use of an alginate oligomer with a further therapeutically active agent (e.g. an anti-microbial or anti-inflammatory agent) may advantageously allow the dose (e.g. the usual or normal dose) of the further therapeutically active agent to be reduced e.g. it may be used at its normal or usual dose or at a lower dose, for example at up to 50% (or at 50%) of its normal dose.

The invention encompasses the use of a single alginate oligomer or a mixture (multiplicity/plurality) of different alginate oligomers. Thus, for example, a combination of different alginate oligomers (e.g. two or more) may be used.

In the case of medical use, the alginates of the invention may be administered to the subject in any convenient form or by any convenient means, e.g. by topical, oral, parenteral, enteral, parenteral routes or by inhalation. Preferably the alginate will be administered by topical, oral or parenteral routes or by inhalation.

The skilled man will be able to formulate the alginates of the invention into pharmaceutical compositions that are adapted for these routes of administration according to any of the conventional methods known in the art and widely described in the literature. Merely for guidance only, Examples 11 and 12 describe two possible compositions (a topical composition and a debridement liquid).

The present invention therefore also provides a pharmaceutical composition for use in treating or preventing a biofilm infection comprising an alginate oligomer as defined herein together with at least one pharmaceutically acceptable carrier, diluent or excipient.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers ointments, soft and hard gelatine capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Preferred excipients and diluents are mannitol and hypertonic salt water (saline).

The compositions may additionally include lubricating agents, wetting agents, emulsifying agents, suspending agents, preserving agents, sweetening agents, flavouring agents, and the like.

As discussed above, the alginate oligomers proposed for use according to the invention may be used in combination with other therapeutic agents, for example to be administered together, in a single pharmaceutical formulation or composition, or separately (i.e. for separate, sequential or simultaneous administration). Thus, the alginates of the invention may be combined with a second (or further) therapeutically active agent, e.g. in a pharmaceutical kit or as a combined ("combination") product.

Thus a further aspect of the present invention provides a product containing an alginate oligomer as defined herein and a second active agent as a combined preparation for separate, simultaneous or sequential application to a biofilm and/or administration to a subject for use in combating biofilm and/or treating or preventing a biofilm infection in a subject or any condition defined herein.

Additional therapeutically active agents may be included in the pharmaceutical compositions, as discussed in relation to combination therapies above Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringers Injection, Dextrose Injection, Dextrose and Sodium Chloride Injection, Lactated Ringers Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

For topical administration the alginate oligomer can be incorporated into creams, ointments, gels, transdermal patches and the like. The alginate oligomers can also be incorporated into medical dressings, for example wound dressings e.g. woven (e.g. fabric) dressings or non-woven dressings (e.g. gels or dressings with a gel component). The use of alginate polymers in dressings is known, and such dressings, or indeed any dressings, may further incorporate the alginate oligomers of the invention.

Accordingly, in a further specific embodiment, the invention further provides a wound dressing comprising an alginate oligomer (which may be any alginate oligomer as herein defined).

Further topical systems that are envisaged to be suitable are in situ drug delivery systems, for example gels where solid, semi-solid, amorphous or liquid crystalline gel matrices are formed in situ and which may comprise the alginate oligomer. Such matrices can conveniently be designed to control the release of the alginate oligomer from the matrix, e.g. release can be delayed and/or sustained over a chosen period of time. Such systems may form gels only upon contact with biological tissues or fluids. Typically the gels are bioadhesive. Delivery to any body site that can retain or be adapted to retain the pre-gel composition can be targeted by such a delivery technique. Such systems are described in WO 2005/023176.

For application to oral, buccal and dental surfaces, toothpastes and mouthwashes are mentioned specifically. Thus, in one particular aspect is included an oral health care, or oral hygiene, composition, comprising an alginate oligomer (which may be any alginate oligomer as defined herein), particularly a mouthwash or toothpaste.

As noted above, a preferred composition of the invention is a debridement composition that is used in a debridement process to remove biofilm, for example from a tissue. Typically such a composition will be liquid, but gels, gel-sols, or semi-solid compositions might be used. The composition might be used to debride the biofilm (e.g. by application to the tissue under pressure) and/or may be used to bathe the tissue before, during and/or after debridement by other means such as by surgical, mechanical or chemical processes. The skilled person is readily able to formulate debridement compositions in accordance with the invention.

In the case of biofilms on an inanimate surface, the alginate oligomer may be applied to the surface to be treated in any convenient composition or formulation, or by any convenient means. Thus the alginate oligomer may be in liquid, gel, gel-sol, semi-solid or solid form (e.g. solutions, suspensions, homogenates, emulsions, pastes, powders, aerosols, vapours). Typically the compositions for treating such inanimate surface biofilms will be a non-pharmaceutically acceptable composition. The choice of composition form will be dictated by the biofilm structure and colony composition and location. For instance, if the location of the biofilm is a fluid line it might be convenient to apply a fluid composition. It might also be preferred to use a composition that persists on the surface to be treated but that will not leach into the fluid of normal use, e.g. an adhesive gel. The skilled person is readily able to prepare suitable compositions from his common general knowledge. For instance, the alginate oligomer may be added to a paint formulation and applied to the surface to be treated, e.g. a boat hull or other part of a boat's structure that is exposed to water, or to a building or any part thereof, a tank (e.g. a storage or processing tank) or indeed to any part of any industrial machinery. Such compositions may conveniently also comprise an anti-microbial agent, as described above, e.g. chlorine bleach, TCP, ethanol, Virkon™, povidone-iodine, silver compounds etc. As the compositions need not be pharmaceutically acceptable, harsher antimicrobials can be used subject to considerations of surface damage, environmental contamination, user safety and contamination of the treated surface and interaction with the other components of the composition.

The compositions of the invention may be formulated so as to provide quick, sustained or delayed release of the active ingredient after administration to the subject/surface by employing procedures well known in the art. Adhesive compositions are also preferred. Adhesive, sustained and/or delayed release formulations may be particularly convenient.

In a further aspect the invention provides products susceptible to biofilm colonisation whose susceptible surfaces have been pretreated with an alginate oligomer as defined herein. Non-limiting examples of products and surfaces susceptible to biofilm colonisation are described above. Particular mention may be made of food or drink processing, storage or dispensing equipment and medical devices. Pretreatment can be achieved by any convenient means, for example any form of applying the alginate oligomer to the surface, notably coating the surface, e.g. spray drying, polymer coating with a polymer incorporating the alginate oligomer, and painting, varnishing or lacquering with paint, varnish or lacquer formulations containing the alginate oligomer. Such a "coating" composition (e.g. a paint, varnish or lacquer) containing an alginate oligomer represents a further aspect of the present invention. Alternatively, the alginate oligomer can be incorporated into the material from with the surface is manufactured. This approach is suited to surfaces manufactured from polymers such as plastics and silicones, e.g. the medical devices described above.

The invention will be further described with reference to the following non-limiting Examples:

EXAMPLES

Example 1

Materials and Standard Methods

Bacterial Strains.

Two culture collection strains *Pseudomonas aeruginosa* PAO1 (ATCC 15682, a wound isolate) and *Staphylococcus aureus* (ATCC 6538) were used for the MBEC assays alongside a clinical isolate from a chronic venous leg ulcer, *S. aureus* (MRSA) '1103'. Two *Candida* type-strains, *C. albicans* ATCC 90028 and *C. dubliniensis* CD36$^T$ were used for the attachment assays.

Chemicals and Bacterial Media.

Bacterial colonies were grown on blood agar base No2, (BA; Lab15, LabM, Bury, UK) supplemented with 5% sheeps' blood and were used to inoculate tryptone soya broth (TSB, CM0129, Oxoid, Basingstoke, UK) for overnight growth. Biofilms were generated in cation-adjusted Mueller-Hinton broth (CAMHB; Lab114, LabM). All antibiotics used were pharmaceutical grade (Sigma-Aldrich, Gillingham, UK) and included amikacin, oxytetracycline and tobramycin. Pig gastric mucin glycoprotein (purified by Jeff Pearson, Newcastle University) and alginate oligomers CF-5/20 ("G-fragments"; 2600 Da, % G 90-95) and G-block #0802 (6400 Da, % G 91) were provided by Algipharma AS, Sandvika, Norway.

Minimum Biofilm Eradication Concentration Assay (MBEC).

The MBEC method used was adapted from Moskowitz S M, et al (2004) J Clin Microbiol 42:1915-1922. After retrieval from −80° C. storage, bacterial isolates were grown on BA and then grown overnight in TSB. After dilution of the bacterial cultures to 0.5 McFarland in CAMHB with or without mucin (2.5 g/l), 100 µl was transferred to the wells of a flat-bottom 96-well microtiter plate. In Example 3, bacterial cultures were diluted to 0.5 McFarland in CAMHB with mucin (2.5 g/l) and alginate and 100 µl was transferred to the wells of a flat-bottom 96-well microtiter plate Plates were then wrapped in parafilm to prevent dehydration and incubated at 37° C. to allow biofilm formation. Incubation times and conditions varied as described below.

After biofilm formation, planktonic cells and supernatant were removed and each well was then washed with sterile phosphate buffered saline (PBS). After washing, cells were treated with combinations of alginates and/or antibiotics with or without mucin (2.5 g/l) in 100 µl CAMHB. Plates were then wrapped in parafilm and incubated at 37° C. with gentle tilting. Incubation times and conditions varied as described below. The antibiotics and concentration ranges used are shown below.

Wells were washed with PBS and 100 µl of each concentration of a serial dilution of antibiotic in CAMHB was then added in duplicate. Plates were again wrapped in parafilm and incubated at 37° C. with gentle tilting overnight.

In all MBEC assays final cell number was assessed as follows. Wells were washed with PBS and biofilms resuspended in 100 µl CAMHB by vigorous pipetting. The optical density at 620 nm (OD$_{620}$) was measured on a microplate reader (FLUOstar OPTIMA, BMG LABTECH) immediately (0 h) and after incubation at 37° C. at 6 h and 24 h.

The MBEC value is that concentration of antibiotic that inhibits all growth of the bacteria in the test sample. Bacterial growth is measured by an increase in the absorbance of the sample. Therefore, a reduction in MBEC value is an indication that the sensitivity of the sample to the antibiotic has been increased (i.e. less antibiotic is needed to prevent bacterial growth).

Antibiotics and Concentration Ranges Used.

| Antibiotic | Concentration range (µg ml$^{-1}$) |
|---|---|
| Amikacin | 4-4096 |
| Amikacin + Oxytetracycline | 4-4096 |
| Oxytetracycline | 4-4096 |
| Tobramycin | 4-4096 |

Minimum Biofilm Eradication Concentration (MBEC) Assay without Mucin.

*Pseudomonas aeruginosa* PAO1 (ATCC 15682) was used to determine MBEC values without the addition of mucin. The MBEC protocol was followed as described above, but without the addition of mucin to the growth medium. Two antibiotics, amikacin and tobramycin were tested.

Yeast Attachment Assay.

The attachment assay used was adapted from Djordjevic et al., (2002) Appl Environ Microbiol 68:2950-2958. *C. albicans* ATCC 90028 and *C. dubliniensis* CD36$^T$ were the *Candida* strains used for the attachment assays. *Candida* were grown on Sabourauds dextrose agar (Lab33, LabM) and overnight broth cultures were grown in Sabouraud liquid medium (Lab9, LabM). After addition of 5 µl overnight culture, 95 µl CAMHB with added mucin (2.5 g/l) and G-fragments (at concentrations of 0, 2%, 6% or 10%) were added to wells. Plates were wrapped in parafilm and incubated at 37° C. overnight to allow biofilm formation.

Planktonic cells and supernatant was removed from the wells before washing the resultant biofilms (3×) with sterile dH$_2$O. Plates were then dried at 56° C. for 45 min. Each well was then stained with 150 µl 1% (v/v) crystal violet (in water) for 45 min. Plates were again washed (3×) with dH$_2$O, before adding 200 µl of 95% ethanol. After 5 min, 100 µl from each well was transferred to a new microtitre plate. OD was then measured on a plate reader at 540 nm.

Growth of Biofilms for Imaging.

After retrieval from −80° C. storage, bacterial isolates were grown on BA and then grown overnight in TSB. After dilution of the bacterial cultures to 0.5 McFarland in CAMHB with mucin (2.5 g/l), 100 it was transferred to the wells of a flat-bottom 96-well microtiter plate. Plates were then wrapped in parafilm to prevent dehydration and incubated at 37° C. for 6 hr to allow biofilm formation. After biofilm formation, planktonic cells and supernatant were removed and each well was then washed with sterile phosphate buffered saline (PBS). After washing, cells were treated with G fragments and mucin (2.5 g/l) in 100 it CAMHB. Plates were then wrapped in parafilm and incubated at 37° C. for 24 hr with gentle tilting.

Scanning Electron Microscopy (SEM) of *Pseudomonas* Biofilms.

Glutaraldehyde (2%) was added to G-fragment treated biofilms and fixed at room temperature for 24 hours. The samples were dehydrated in a graded series of ethanol concentrations, dried in a critical point dryer (Balzers CPD 030, Germany), mounted on aluminium stubs, coated with gold in a sputter-coater (EMscope model AE 1231, UK), and then viewed on a scanning electron microscope (FEI-Philips XL-20, The Netherlands).

Confocal Microscopy of Undisturbed Biofilms Using or BODIPY® 630/650-X SE

G-fragment treated biofilms were washed with sterile distilled water and stained with the BODIPY® 630/650-X SE stain (BODIPY® 630/650-X SE, Invitrogen Ltd) which selectively stains the matrix components (EPS) in *Pseudomonas* biofilms.

BODIPY® 630/650-X SE was added (100 µl (10 µg/ml)) to each biofilm sample. The preparation was incubated in the dark for 1 hour and then analysed by CLSM.

Example 2

Figure 2:
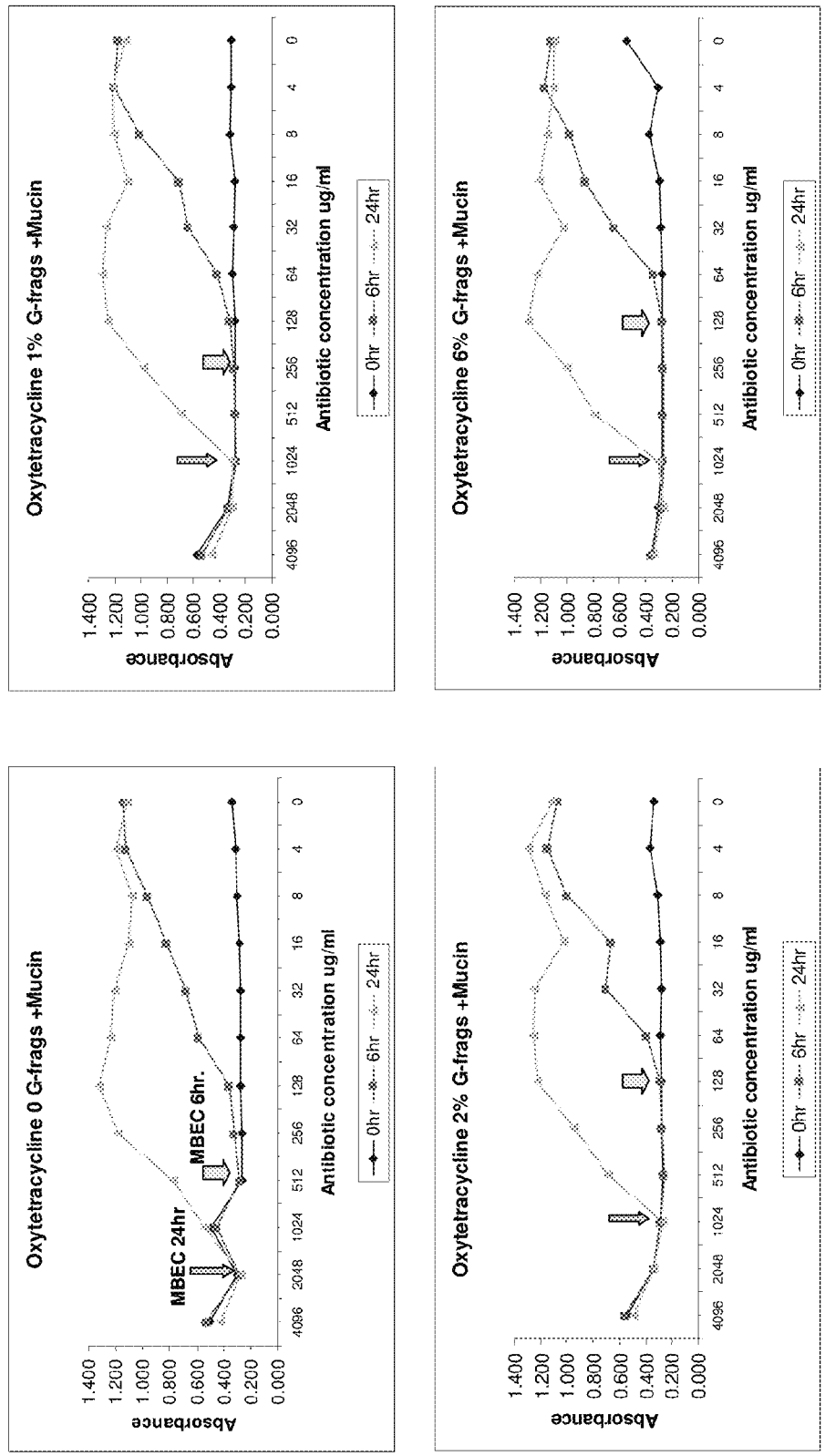
FIG. 2 shows bacterial growth in *Pseudomonas* biofilms, generated overnight and then treated with mucin (2.5 g/L) and G-fragments (0, 1%, 2% or 6%) overnight, at 0 hr, 6 hr and 24 hr after overnight treatment with oxytetracycline (4096-0 mg/ml).

Measurement of MBEC Values for Overnight *Pseudomonas Aeruginosa* Biofilms Pretreated with G-Fragments The MBEC assay described above was followed. Biofilms were generated in plates overnight without mucin. Following a PBS wash, the biofilms were incubated with 0, 1, 2 or 6% G-fragments and mucin overnight. After washing with PBS cells were incubated overnight with antibiotics (amikacin or oxytetracycline) and without mucin. Results are shown graphically in FIGS. 1 and 2 and tabulated in Tables 2 and 3 below. As can be seen, overnight pretreatment of biofilm with G fragments causes reductions in 6 hr and 24 hr MBEC values for amikacin or oxytetracycline. 6 hr MBEC values for amikacin and oxytetracycline were halved by 1% G fragments and quartered by 2 and 6% G fragments. 24 hr MBEC values for oxytetracycline were halved by all concentrations of G fragments. 24 hr MBEC values for amikacin were reduced although it was not possible to quantify this reduction. This indicates that an overnight pretreatment with G fragments increases the sensitivity of *Pseudomonas aeruginosa* in biofilms to these antibiotics.

TABLE 2

Summary of MBEC values at 6 hours after overnight exposure to antibiotic. *Pseudomonas* biofilms generated overnight. Mucin (2.5 g/L) and G-fragments at 0, 1%, 2% or 6% were added to established biofilms. Values expressed as µg/ml of antibiotic.

| [G-FRAG] | Amikacin | Oxytetracycline |
|---|---|---|
| 0 | 2048 | 512 |
| 1% | 1024 | 256 |
| 2% | 512 | 128 |
| 6% | 512 | 128 |

TABLE 3

Summary of MBEC values at 24 hours after overnight exposure to antibiotic. *Pseudomonas* biofilms generated overnight. Mucin (2.5 g/L) and G-fragments at 0, 1%, 2% or 6% added to established biofilms. Values expressed as µg/ml of antibiotic.

| [G-FRAG] | Amikacin | Oxytetracycline |
|---|---|---|
| 0 | >4096 | 2048 |
| 1% | 4096 | 1024 |
| 2% | 4096 | 1024 |
| 6% | 4096 | 1024 |

Key
Decrease in MBEC value from 0% G

Example 3

Figure 3:
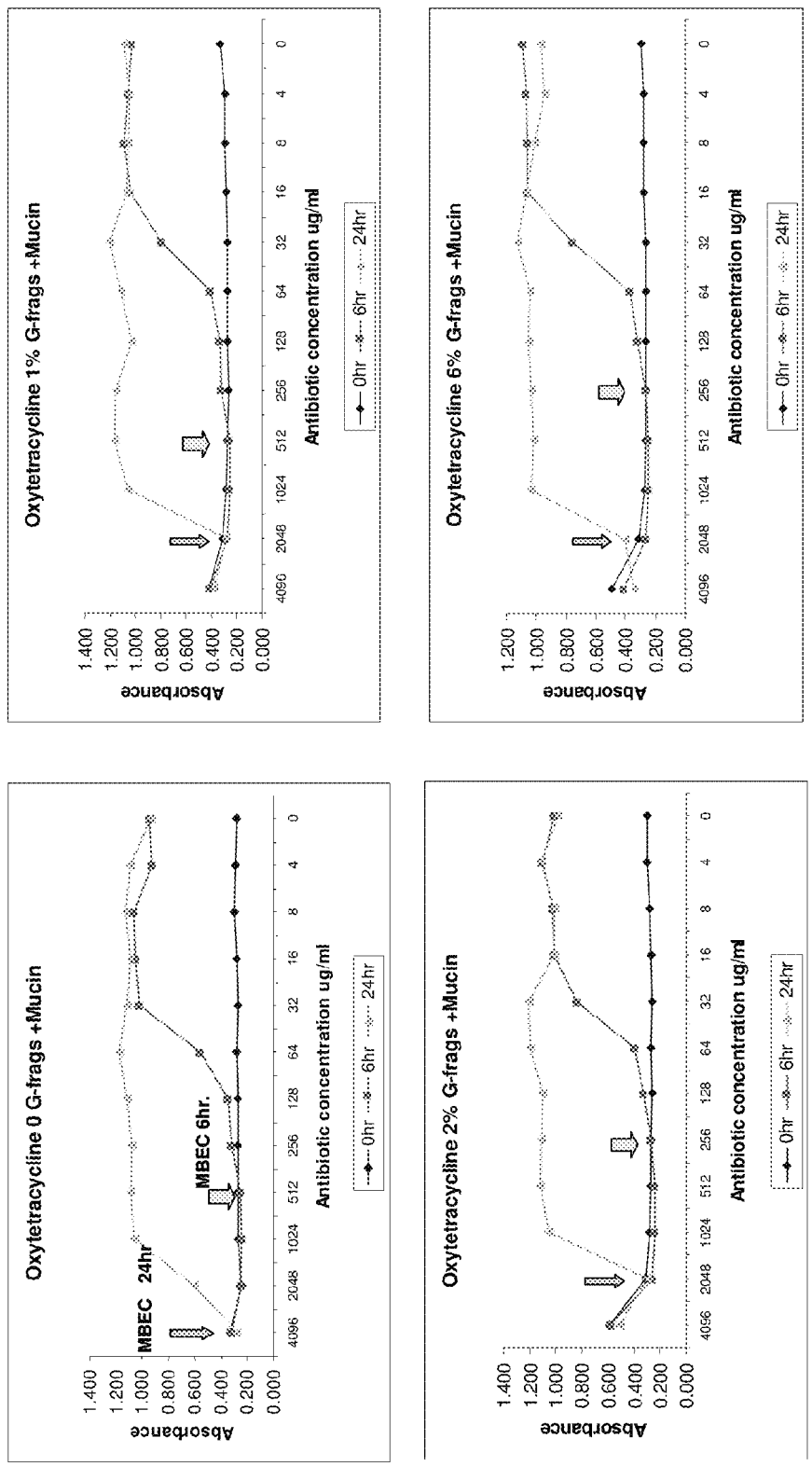
FIG. 3 shows bacterial growth in *Pseudomonas* biofilms generated with mucin (2.5 g/L) and G-fragments (0, 1%, 2% or 6%) overnight, at 0 hr, 6 hr and 24 hr after overnight treatment with oxytetracycline (4096-0 µg/ml).

Measurement of MBEC Values for *Pseudomonas aeruginosa* Biofilms Generated in the Presence of G-Fragments The MBEC assay described above was followed. Biofilms were generated in plates overnight in the presence of mucin and 0, 1, 2 or 6% G fragments. After washing, biofilms were exposed to oxytetracycline (without mucin) overnight. Results are shown graphically in FIG. 3 and tabulated in Tables 4 and 5 below. As can be seen, at all concentrations of G fragments tested, generating biofilms in the presence of G-fragments halved 24 hr MBEC values. 6 hr MBEC values were halved when 2% and 6% G fragments were used. 1% G fragments failed to cause a reduction. These data show that *Pseudomonas aeruginosa* in biofilms generated in the presence of G fragments are more susceptible to oxytetracycline than *Pseudomonas aeruginosa* in biofilms generated in the absence of G fragments.

TABLE 4

Summary of MBEC values at 6 hr after overnight exposure to antibiotic. *Pseudomonas* biofilms generated with mucin (2.5 g/L) and G-fragments at 0, 1%, 2% or 6%. Values expressed as µg/ml of antibiotic.

| [G-FRAG] | Oxytetracycline |
|---|---|
| 0 | 512 |
| 1% | 512 |
| 2% | 256 |
| 6% | 256 |

TABLE 5

Summary of MBEC values at 24 hr after overnight exposure to antibiotic. *Pseudomonas* biofilms generated with mucin (2.5 g/L) and G-fragments at 0, 1%, 2% or 6%. Values expressed as µg/ml of antibiotic.

| [G-FRAG] | Oxytetracycline |
|---|---|
| 0 | 4096 |
| 1% | 2048 |
| 2% | 2048 |
| 6% | 2048 |

Key
Decrease in MBEC value from 0% G
No change in MBEC value from 0% G

Example 4

Figure 4:
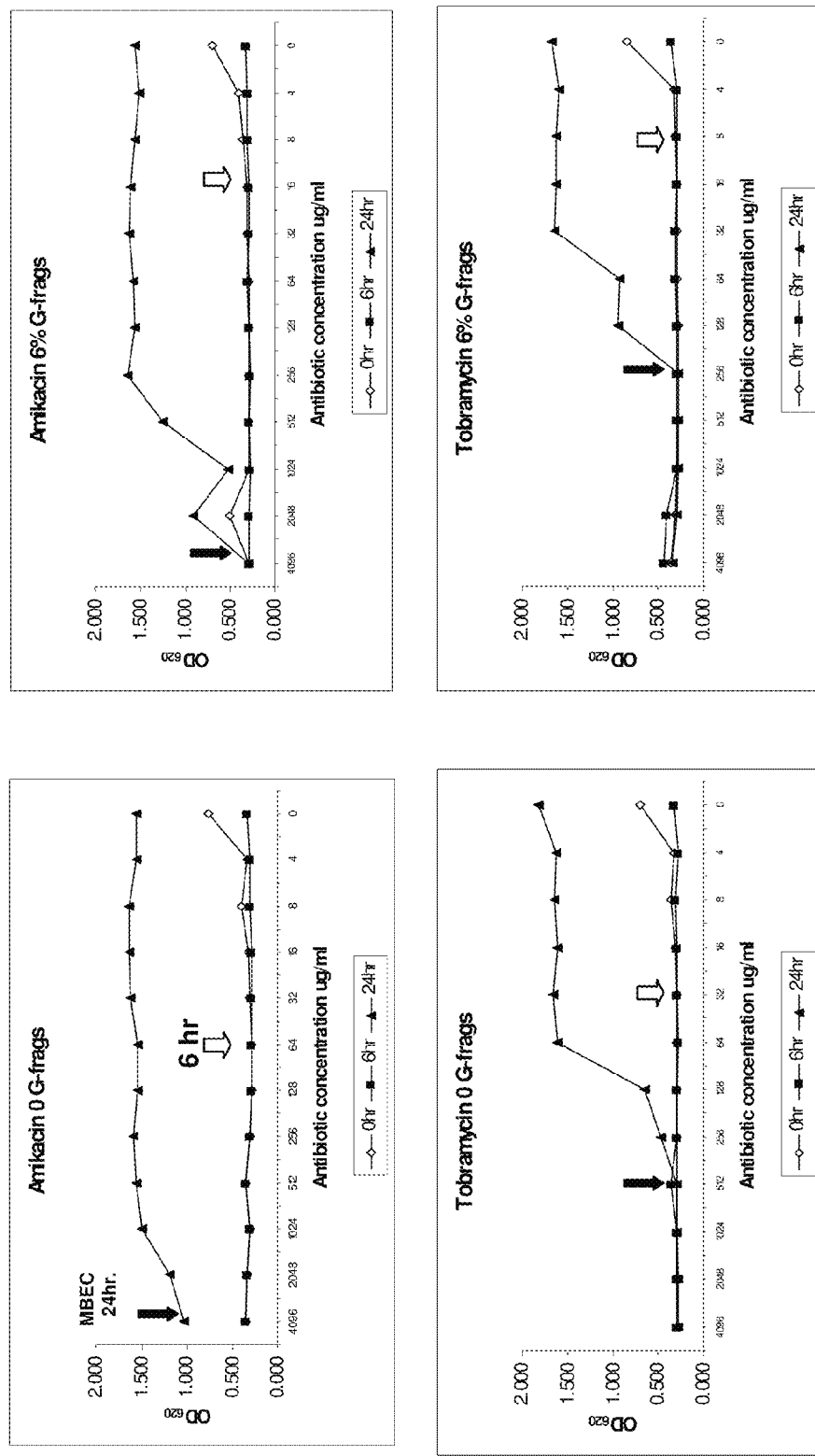
FIG. 4 shows bacterial growth in *Pseudomonas* biofilms, generated with mucin (2.5 g/l) for 6 h and then treated with mucin (2.5 g/L) and G-fragments (0 or 6%) overnight, at 0, 6 and 24 hr after overnight treatment with amikacin, tobramycin, oxytetracycline or 'amikacin+oxytetracycline' (4096-0 µg ml$^{-1}$).
Figure 4:
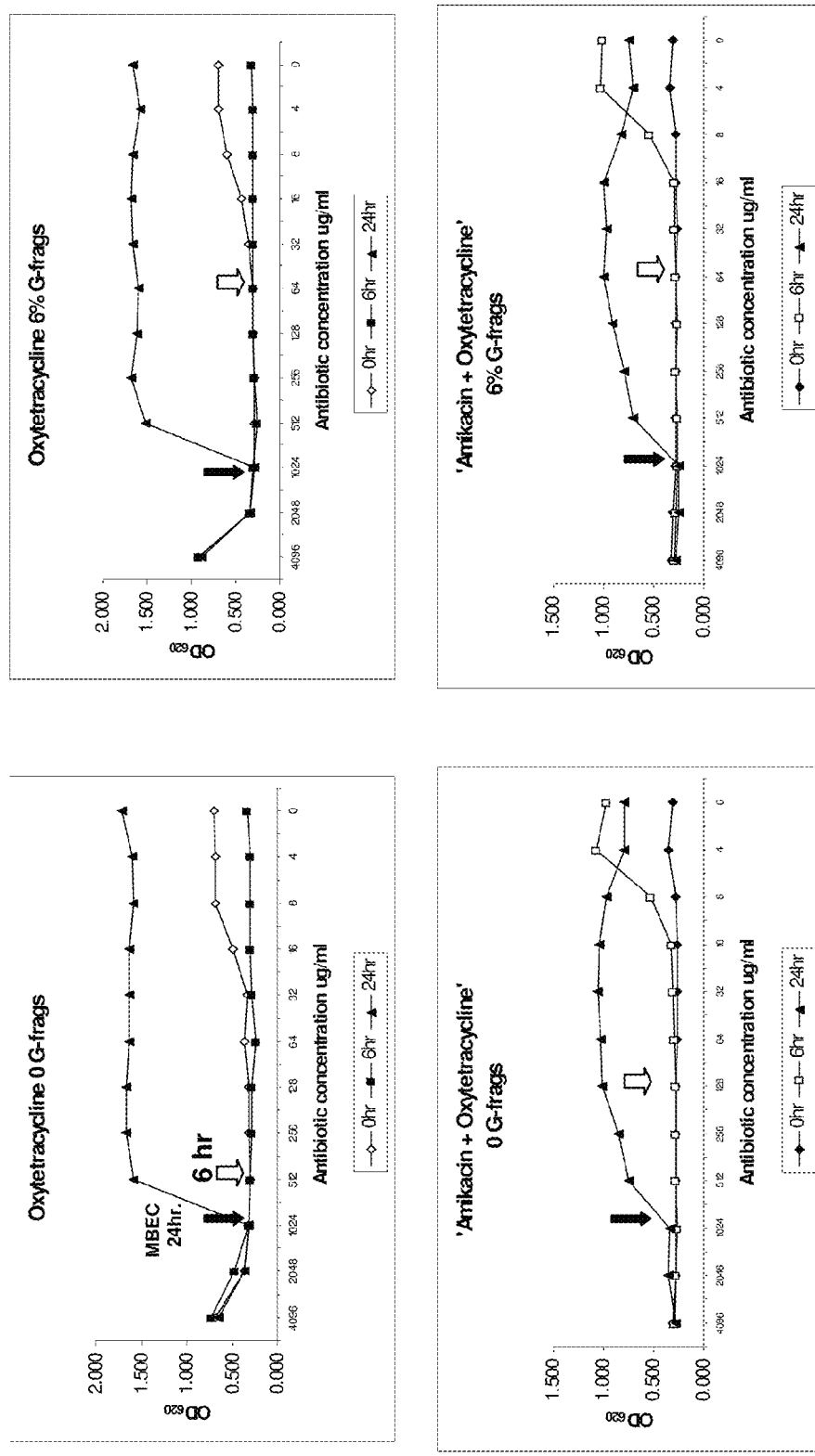

Measurement of MBEC Values for *Pseudomonas aeruginosa* Biofilms Generated for 6 Hr and Pretreated with G-Fragments The MBEC assay described above was followed with mucin present throughout. Biofilms were generated in the presence of mucin during a 6 hour incubation, washed and incubated with G-fragments and mucin overnight. After washing with PBS the cultures were exposed to antibiotics (amikacin, tobramycin, oxytetracycline or a combination of amikacin and oxytetracycline) without mucin. Results are shown graphically in FIG. 4 and in tabulated form in Tables 6 and 7. As can be seen, pretreatment of 6 hr biofilms with 6% G fragments caused the 6 hr MBEC values for all antibiotics tested to at least quarter, i.e. sensitivity of *Pseudomonas aeruginosa* in these biofilm to these antibiotics was at least quadrupled. In fact, 6% G fragments caused a the 6 hr MBEC value for oxytetracycline to drop to ⅛th of the control value. The 24 hr MBEC values for amikacin and tobramycin were halved. The 24 hr MBEC value for oxytetracycline and the amikacin/oxytetracycline mixture showed no change in MBEC values.

TABLE 6

Summary of MBEC values at 6 hr after overnight exposure to antibiotic. *Pseudomonas* biofilms, generated in media with added mucin for 6 hr, exposed to 0 or 6% G-fragments overnight and then exposed to antibiotics. Values expressed as µg ml$^{-1}$ of antibiotic.

| [G-FRAG] | Amikacin | Oxytetracycline | Tobramycin | Amik + Oxy |
|---|---|---|---|---|
| 0 | 64 | 512 | 32 | 128 |
| 6% | 16 | 64 | 8 | 64 |

TABLE 7

Summary of MBEC values at 24 hr after overnight exposure to antibiotic. *Pseudomonas* biofilms generated in media with added mucin for 6 hr, exposed to 0 or 6% G-fragments overnight and then exposed to antibiotics. Values expressed as µg/ml of antibiotic.

| [G-FRAG] | Amikacin | Oxytetracycline | Tobramycin | Amik + Oxy |
|---|---|---|---|---|
| 0 | >4096 | 1024 | 512 | 1024 |
| 6% | 4096 | 1024 | 256 | 1024 |

Key
Decrease in MBEC value from 0% G
No change in MBEC value from 0% G

Example 5

Figure 5:
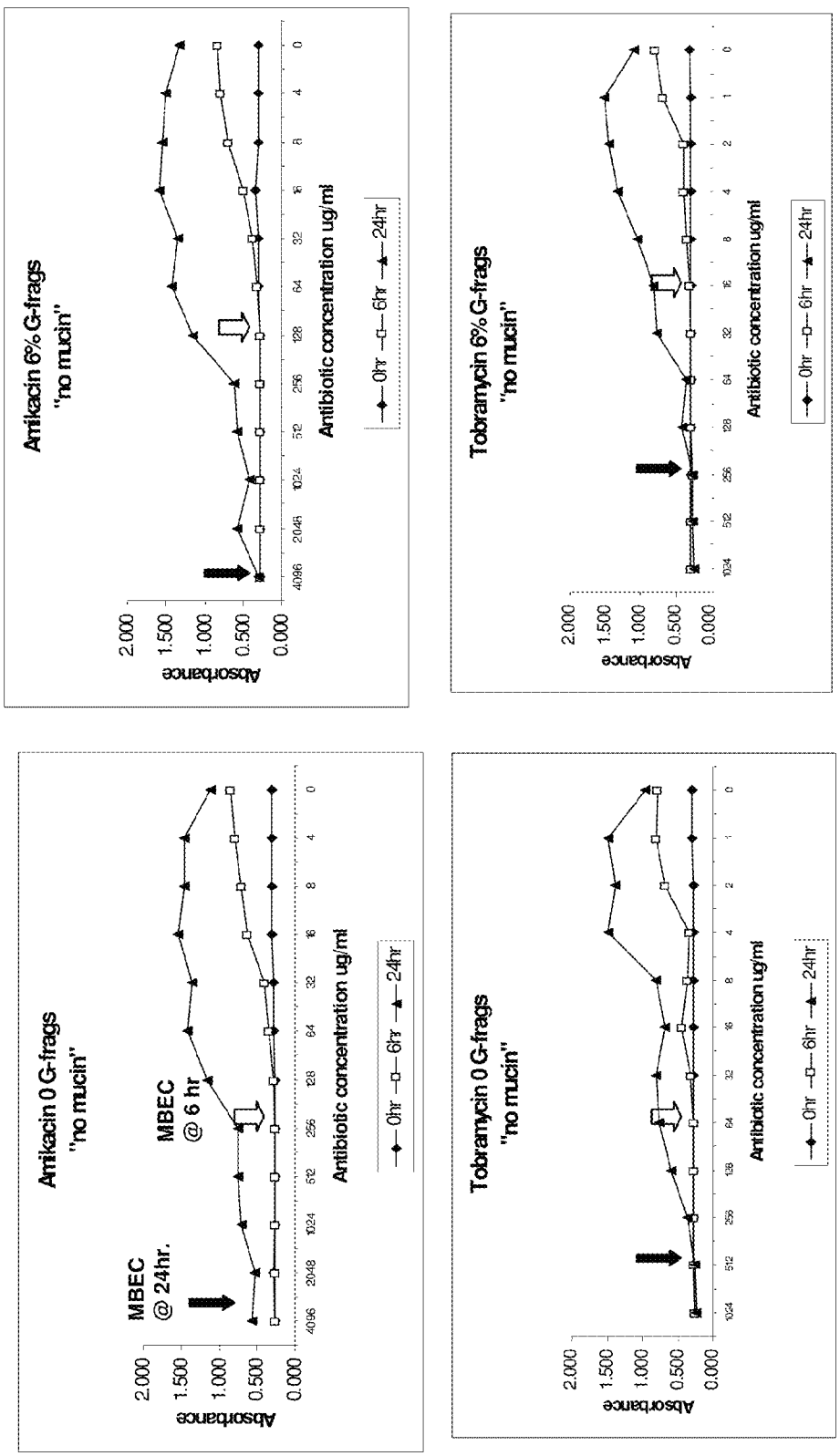
FIG. 5 shows bacterial growth in *Pseudomonas* PAO1 biofilms, generated for 6 h without mucin and then treated with G-fragments (0 or 6%) without mucin, at 0 hr, 6 hr and 24 hr after overnight treatment with amikacin (4096-0 µg/ml) or tobramycin (1024-0 µg/ml).
Figure 6:
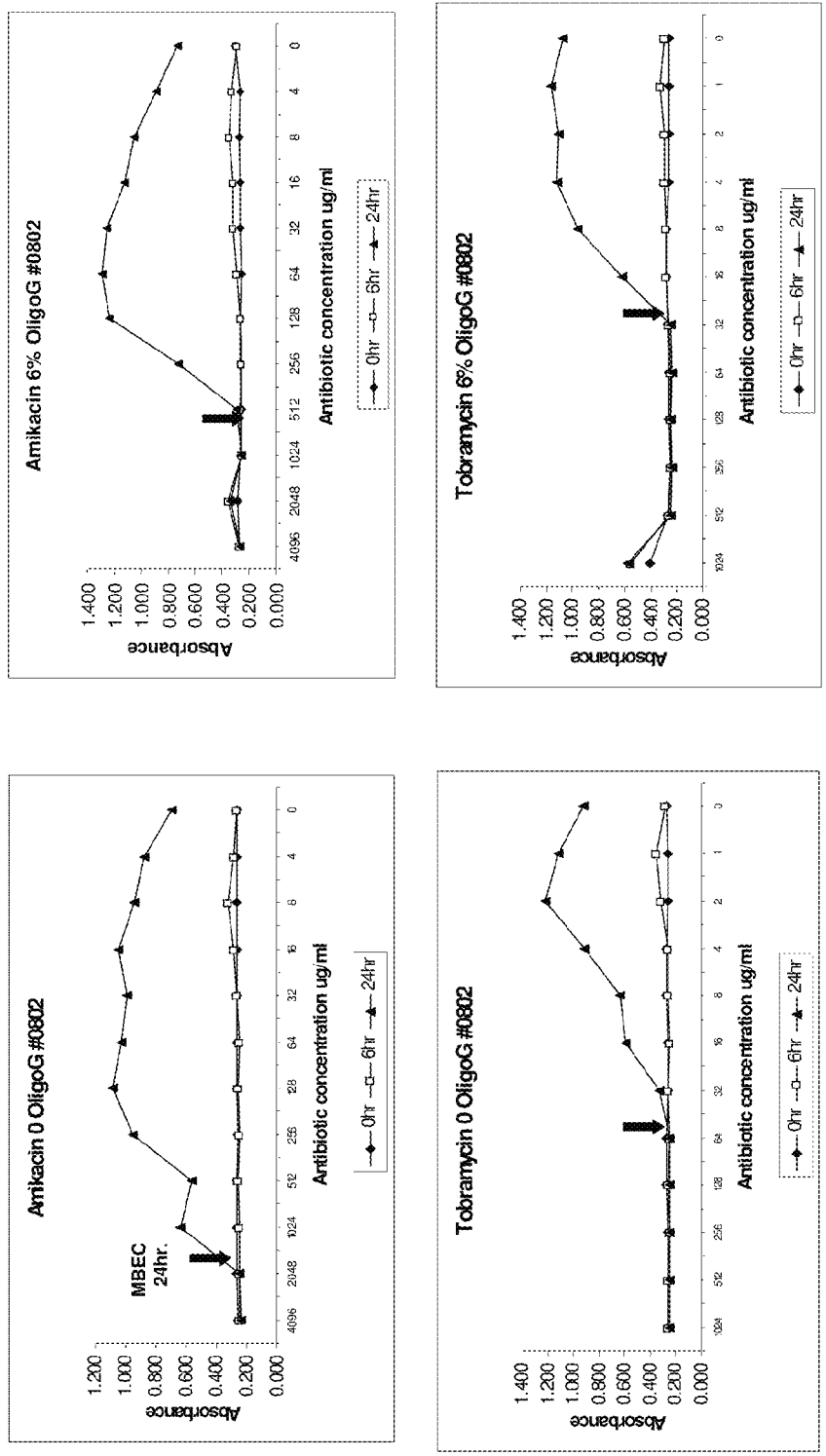
FIG. 6 shows bacterial growth in *Pseudomonas* PAO1 biofilms, generated with mucin (2.5 g/l) for 6 h and then treated with mucin (2.5 g/L) and 'G-block #0802' (0 or 6%) overnight, at 0, 6 and 24 hr after overnight treatment with amikacin (4096-0 µg ml$^{-1}$) or tobramycin (1024-0 µg ml$^{-1}$).

Measurement of MBEC Values for *Pseudomonas aeruginosa* Biofilms Generated for 6 Hr without Mucin and Pretreated with G-Fragments without Mucin The protocol of Example 4 was repeated using tobramycin and amikacin but without the addition of mucin. Results are shown in FIG. 5. As can be seen, in the absence of mucin the G-fragments were still able to halve MBEC values in all but the 24 hr MBEC values for amikacin. This is an indication that mucin is not playing a significant role in the effects seen in the Examples above.

Example 6

Measurement of MBEC Values for *Pseudomonas aeruginosa* Biofilms Generated for 6 Hr and Pretreated with a Different Alginate Oligomer The MBEC assay described in Example 4 was repeated with an alternative alginate oligomer, G-block (#0802) (6400 MW, compared to CF-5/20 G-fragments, 2600 MW) and using tobramycin and amikacin. The MBEC value at 24 hr for amikacin is quartered by pretreatment of the biofilm with 6% G-block (#0802). The same treatment resulted in the 24 hr MBEC value for tobramycin halving. These data show that an another alginate oligomer can elicit an increase in the sensitivity of *Pseudomonas aeruginosa* PA01 in biofilms to tobramycin and amikacin.

Example 7

Figure 7:
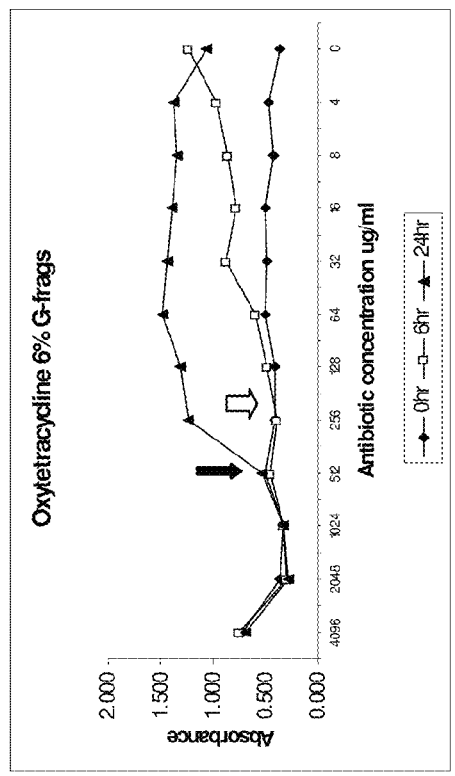
FIG. 7 shows bacterial growth in *Staphylococcus aureus* strain ATCC 6538 biofilms, generated with mucin (2.5 g/l) for 6 h and then treated with mucin (2.5 g/L) and G-fragments (0 or 6%) overnight, at 0, 6 and 24 hr after overnight treatment with oxytetracycline (4096-0 µg ml$^{-1}$).
Figure 7:
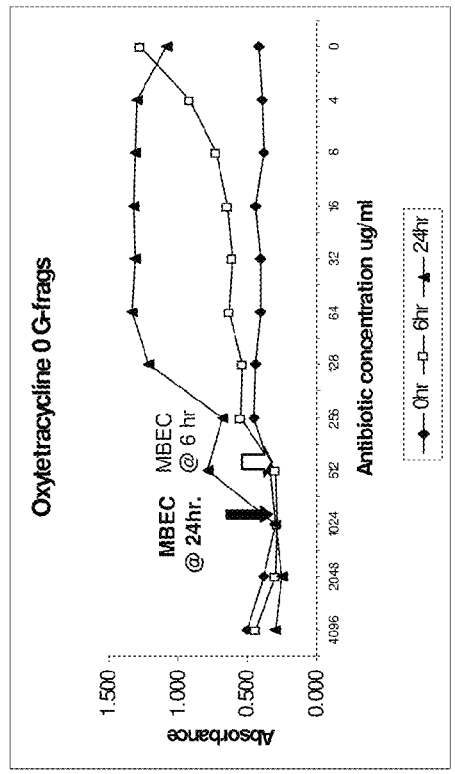
Figure 8:
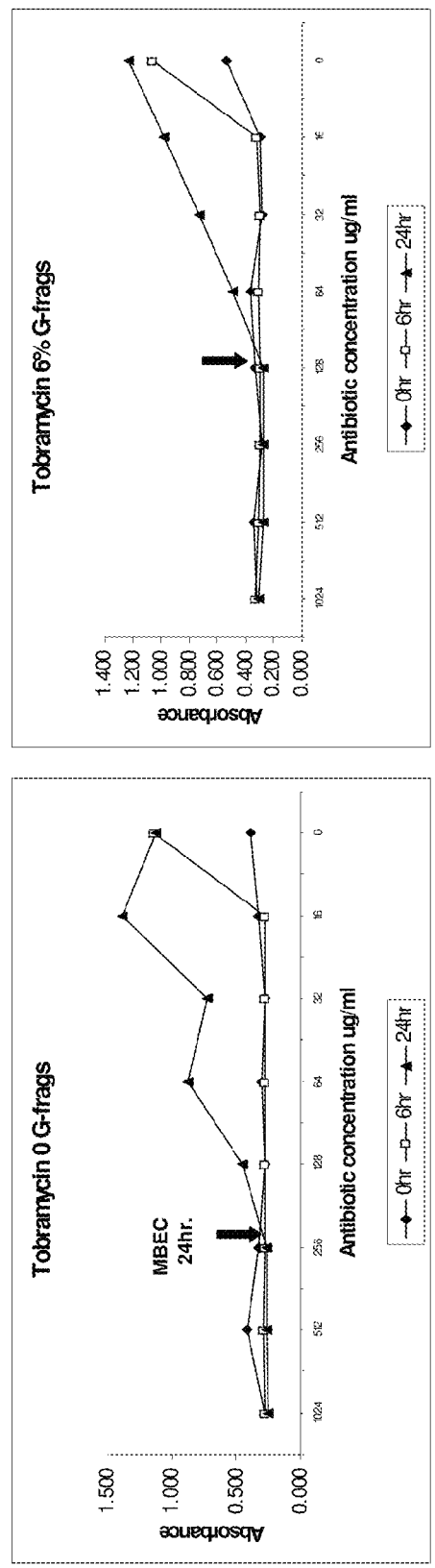
FIG. 8 shows bacterial growth in MRSA wound isolate '1103' biofilms, generated with mucin (2.5 g/L) for 6 h and then treated with mucin (2.5 g/L) and G-fragments (0 or 6%) with added overnight, at 0 hr, 6 hr and 24 hr after overnight treatment with tobramycin (1024-0 µg/ml).

Measurement of MBEC Values for 6 Hr Biofilms Containing Other Bacteria Pretreated with G-Fragments The effect of G-fragments on biofilms of *Staphylococcus aureus* was investigated using the MBEC assay described in Example 4 and oxytetracycline. As can be seen in FIG. 7, pretreatment of biofilms containing *S. aureus* ATCC 6538 with 6% G fragments halved the MBEC values at 6 and 24 hr for oxytetracycline. As can be seen in FIG. 8, pretreatment of biofilms containing the MRSA wound isolate '1103' with 6% G fragments halved the MBEC value at 24 hr for tobramycin. These data show that other bacteria commonly found in biofilms, can be made more susceptible to oxytetracycline and tobramycin by pretreating those biofilms with G fragments.

Example 8

The Effect of G-Fragments on Yeast Attachment in Biofilm

Figure 9:
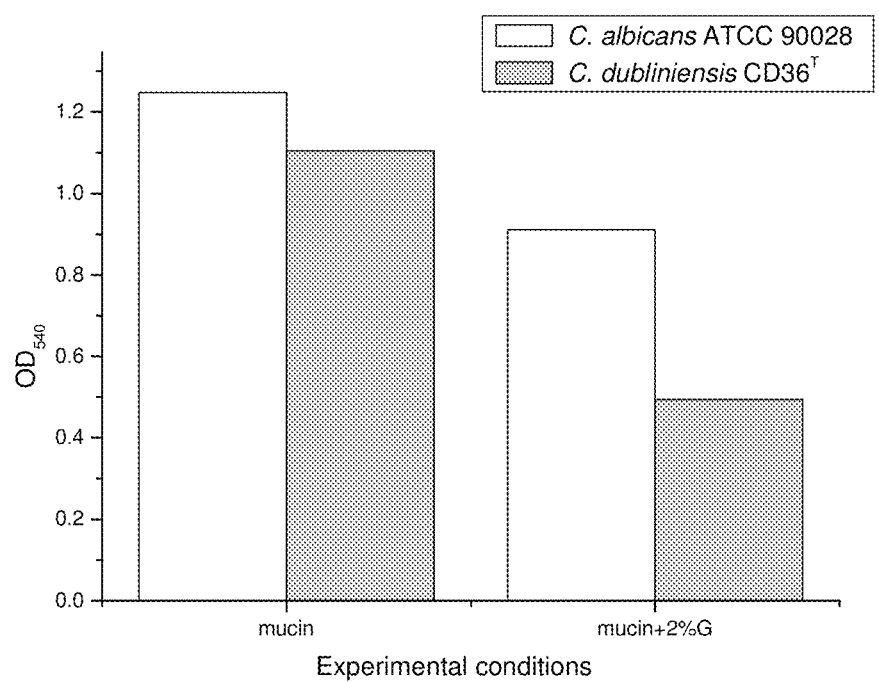
FIG. 9 shows the effect of G-fragments and mucin on the attachment of *Candida albicans* ATCC 90028 and *Candida dubliniensis* CD36$^T$ in biofilms generated with mucin (2.5 g/L) and G-fragments at 0 or 2% overnight.

The effect of G-fragments on attachment of *Candida albicans* and *Candida dubliniensis* in biofilm was investigated using the attachment assay described above. A decrease in attachment of both *Candida* species was observed when biofilms containing these yeasts were formed in the presence of 2% G-fragments and mucin compared to the mucin only control. (FIG. 9). These data show that G fragments can affect the attachment of yeast cells in developing biofilms.

Example 9

Figure 10:
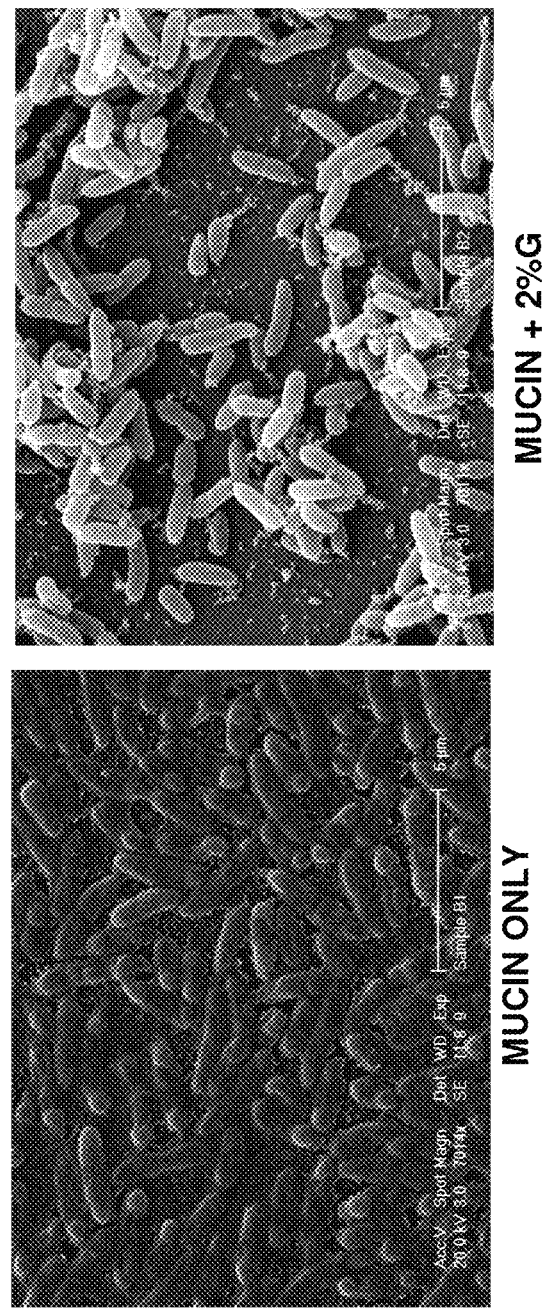
FIG. 10 shows electron micrographs of *Pseudomonas* biofilms generated with mucin (2.5 g/l) for 6 hr and then treated with mucin (2.5 g/L) and G-fragments at 0 or 2% for 24 hr.

Microscopic Analysis of *Pseudomonas* Biofilm Structure and Effects of G-Fragments The overall structure of *Pseudomonas* biofilms was followed using Scanning Electron Microscopy (SEM) FIG. 10 shows the effect of 2% G fragments on biofilm structure. The extracellular polysaccharide (EPS) coating the cell surfaces appears to be disrupted with 2% G-fragments.

Example 10

Microscopic Analysis of *Pseudomonas* Biofilm Structure and Effects of G-Fragments The effect of G fragments on the structure of the *Pseudomonas* biofilm matrix was investigated using confocal microscopy of undisturbed biofilms labelled with the fluorescent dye BODIPY® 630/650-X SE. This dye selectively stains the matrix components (EPS) in *Pseudomonas* biofilms. Subtle fragmentation of the biofilm matrix was apparent with increasing concentration of G-fragments when compared with 'mucin only' control.

Example 11

Topical Composition Comprising Alginate Oligomer

An example of a topical composition (a moisturising skincare body lotion) comprising an alginate oligomer is prepared with the following ingredients.

| Oil phase: | |
|---|---|
| Mineral oil | 3% |
| Cyclomethicone | 4% |
| Isopropyl myristate | 3% |
| Stearic acid | 1.8% |
| Cetyl alcohol | 1.0% |
| Glyceryl stearate | 1.5% |

| Water phase: | |
|---|---|
| Carbomer 984 | 0.10% |
| Glycerine | 3% |
| Thriethanolamine | 0.90% |
| Alginate oligomer | 0.1% |
| Water | 81.60% |

Example 12

Debridement Composition Comprising Alginate Oligomer

An example of a liquid debridement composition comprising an alginate oligomer is prepared with the following ingredients.

| | |
|---|---|
| Castor oil | 77.8% |
| Balsam of Peru refined grade | 10% |
| Collagenase | 0.2% |
| ZnCl$_2$ | 0.5% |
| Water | 5% |
| Polyoxyethylene (10)oleyl ether | 4% |
| Colloidal silica | 2% |
| Alginate oligomer | 0.5% |

What is claimed is:

1. A method for reducing or eliminating a biofilm comprising one or more undesirable microorganisms which is present in or on a human or non-human animal subject, said method consisting of:
    (a) determining the presence of said biofilm in said subject and thereby diagnosing said subject as being in need of said reduction or elimination,
    (b) contacting said biofilm, or a surface or interface with which said biofilm has close interaction, with an alginate oligomer that has 3-35 residues, wherein at least 70% of the residues are G residues, wherein G is an α-L-guluronic acid derived monomer unit, and optionally one or more additional therapeutically effective agents or biofilm disrupting agents, and
    optionally:
    (c) assessing an effect of said alginate oligomer on said biofilm and/or on a condition of said subject or monitoring the size, structure, integrity and/or colony number of said biofilm.

2. A method for reducing or eliminating a biofilm comprising one or more undesirable microorganisms which is present in or on a human or non-human animal subject, wherein said biofilm is not present on or does not interact with a mucosal surface having a hyperviscous mucus coating, said method consisting of:
    (a) contacting said biofilm, or a surface or interface with which said biofilm has close interaction, with an alginate oligomer that has 3-35 residues, wherein at least 70% of the residues are G residues, and optionally one or more additional therapeutically effective agents or biofilm disrupting agents, and optionally:

(b) assessing an effect of said alginate oligomer on said biofilm and/or on a condition of said subject or monitoring the size, structure, integrity and/or colony number of said biofilm.

3. The method of claim 1 wherein the number of monomers in the alginate oligomer is 3-28, 4-25, 6-22 or 8-20.

4. The method of claim 1, wherein the alginate oligomer has at least 80%, 85% or 90% G residues.

5. The method of claim 1, wherein the alginate oligomer has a primary structure in which at least 90% of the G residues are linked 1-4 to another G residue.

6. The method of claim 1, wherein the biofilm is in or on an internal or external body surface or interface selected from the group consisting of a surface in an oral cavity, a reproductive tract, a urinary tract, a respiratory tract, a gastrointestinal tract, a peritoneum, a a middle ear or a prostate; vascular intima; conjunctiva; corneal tissue; lung tissue; heart valves; skin; scalp; nails; teeth and an interior of a wound.

7. The method of claim 1, wherein the subject is selected from the group consisting of a subject coincidentally also suffering from a different pre-established infection, an immunocompromised subject, a subject also undergoing intensive or critical care, a subject also suffering from trauma, a subject also suffering from a burn, a subject also suffering from an acute and/or chronic wound, a neonatal subject, an elderly subject, a subject also suffering from a malignant neoplasm, a subject also suffering from a non-malignant neoplasm, a subject also suffering from an autoimmune condition, a subject also suffering from reduced or abrogated epithelial or endothelial secretion and/or secretion clearance and a subject also fitted with a medical device.

8. The method of claim 1, wherein the subject is selected from the group consisting of a subject coincidentally also suffering from a condition selected from the group consisting of human immunodeficiency virus (HIV), sepsis, septic shock, acquired immunodeficiency syndrome (AIDS), leukemia, a lymphoma, rheumatoid arthritis, diabetes mellitus type I, Crohn's disease, chronic obstructive pulmonary disease (COPD), bronchitis, cystic fibrosis, emphysema, lung carcinoma, asthma, pneumonia and sinusitis, a subject preparing for, undergoing, or recovering from chemotherapy, radiotherapy, or an organ transplant, a resident in a healthcare institution and a smoker.

9. The method of claim 1 wherein the method is for treating dental plaque, gingivitis, periodontitis, native valve endocarditis, acute otitis media, chronic bacterial prostatitis, pneumonia, asthma or device-related infection resulting from implantable and/or prosthetic medical devices or tissue replacements.

10. The method of claim 1, wherein the one or more additional therapeutically effective agents or biofilm disrupting agents are selected from the group consisting of an anti-microbial agent, an immunostimulatory agent, a growth factor and an anti-inflammatory agent.

11. The method of claim 10, wherein the anti-microbial agent is selected from the group consisting of an antibiotic, an anti-fungal agent, an antiseptic, a disinfectant, a sterilizing agent and a cleaning agent.

12. The method of claim 1, wherein the one or more additional therapeutically effective agents or biofilm-disrupting agents are selected from the group consisting of proteases, nucleases, lipases, enzymes capable of degrading polysaccharides, gelsolin, thiol reducing agents, an acetylcysteine, an uncharged polysaccharide, an anionic polyamino acid and a mucosal viscosity-reducing agent selected from the group consisting of nucleases, lipases, enzymes capable of degrading polysaccharides, gelsolin, thiol reducing agents, an acetylcysteine, sodium chloride, an uncharged polysaccharide, an anionic polyamino acid, a nitric oxide precursor or synthesis stimulator, ambroxol, bromhexine, carbocisteine, domidol, epazinone, erdosteine, letosteine, mesna, neltenexin, sobresol, strepronin and tiopronin.

13. The method of claim 12, wherein said additional biofilm-disrupting agents or the mucosal viscosity-reducing agent is an alginate lyase and/or a DNase enzyme.

14. The method of claim 2, wherein the number of monomers in the alginate oligomer is 3-28, 4-25, 6-22 or 8-20.

15. The method of claim 2, wherein the alginate oligomer has at least 80%, 85% or 90% G residues.

16. The method of claim 2, wherein the alginate oligomer has a primary structure in which at least 90% of the G residues are linked 1-4 to another G residue.

17. The method of claim 2, wherein the biofilm is in or on an internal or external body surface or interface selected from the group consisting of a surface in an oral cavity, a reproductive tract, a urinary tract, a respiratory tract, a gastrointestinal tract, a peritoneum, a middle ear or a prostate; vascular intima; conjunctiva; corneal tissue; lung tissue; heart valves; skin; scalp; nails; teeth and an interior of a wound.

18. The method of claim 2, wherein the subject is selected from the group consisting of a subject coincidentally also suffering from a different pre-established infection, an immunocompromised subject, a subject also undergoing intensive or critical care, a subject also suffering from trauma, a subject also suffering from a burn, a subject also suffering from an acute and/or chronic wound, a neonatal subject, an elderly subject, a subject also suffering from a malignant neoplasm, a subject also suffering from a non-malignant neoplasm, a subject also suffering from an autoimmune condition, a subject also suffering from reduced or abrogated epithelial or endothelial secretion and/or secretion clearance and a subject also fitted with a medical device.

19. The method of claim 2, wherein the subject is selected from the group consisting of a subject coincidentally also suffering from a condition selected from the group consisting of human immunodeficiency virus (HIV), sepsis, septic shock, acquired immunodeficiency syndrome (AIDS), leukemia, a lymphoma, rheumatoid arthritis, diabetes mellitus type I, Crohn's disease, chronic obstructive pulmonary disease (COPD), bronchitis, cystic fibrosis, emphysema, lung carcinoma, asthma, pneumonia and sinusitis, a subject preparing for, undergoing, or recovering from chemotherapy, radiotherapy, or an organ transplant, a resident in a healthcare institution and a smoker.

20. The method of claim 2, wherein the method is for treating dental plaque, gingivitis, periodontitis, native valve endocarditis, acute otitis media, chronic bacterial prostatitis, pneumonia, asthma or device-related infection resulting from implantable and/or prosthetic medical devices or tissue replacements.

21. The method of claim 2, wherein the one or more additional therapeutically effective agents or biofilm disrupting agents are selected from the group consisting of an anti-microbial agent, an immunostimulatory agent, a growth factor and an anti-inflammatory agent.

22. The method of claim 21, wherein the anti-microbial agent is selected from the group consisting of an antibiotic, an anti-fungal agent, an antiseptic, a disinfectant, a sterilizing agent and a cleaning agent.

23. The method of claim 2, wherein the one or more additional therapeutically effective agents or biofilm-disrupting agents are selected from the group consisting of proteases, nucleases, lipases, enzymes capable of degrading polysaccharides, gelsolin, thiol reducing agents, an acetylcysteine, an uncharged polysaccharide, an anionic polyamino acid and a mucosal viscosity-reducing agent selected from the group consisting of nucleases, lipases, enzymes capable of degrading polysaccharides, gelsolin, thiol reducing agents, an acetylcysteine, sodium chloride, an uncharged polysaccharide, an anionic polyamino acid, a nitric oxide precursor or synthesis stimulator, ambroxol, bromhexine, carbocisteine, domidol, epazinone, erdosteine, letosteine, mesna, neltenexin, sobresol, strepronin and tiopronin.

24. The method of claim 23, wherein said one or more additional therapeutically effective agents or biofilm-disrupting agents or the mucosal viscosity-reducing agent are an alginate lyase and/or a DNase enzyme.

25. The method of claim 1, wherein the alginate oligomer has an average molecular weight of less than 6,000 Daltons.

26. The method of claim 2, wherein the alginate oligomer has an average molecular weight of less than 6,000 Daltons.

27. A method for reducing or eliminating a biofilm comprising one or more microorganisms, which is present in or on a human or non-human animal subject, wherein said biofilm has close interaction with or is on a surface or interface of the subject's respiratory tract, gastrointestinal tract, reproductive tract, urinary tract, peritoneum, middle ear, prostate, conjunctiva, cornea or heart valve, said method consisting of:
(a) determining the presence of said biofilm in said subject and thereby diagnosing said subject as being in need of said reduction or elimination, and
(b) contacting said biofilm, or said surface or interface with which said biofilm has close interaction, with an alginate oligomer of 3-35 monomer residue of which at least 70% are G residues and optionally one or more additional therapeutically effective agents or biofilm disrupting agents, and
optionally:
(c) assessing an effect of said alginate oligomer on said biofilm and/or on a condition of said subject or monitoring the size, structure, integrity and/or colony number of said biofilm.

* * * * *